United States Patent
Montagu et al.

(10) Patent No.: US 7,154,598 B2
(45) Date of Patent: Dec. 26, 2006

(54) EXCITATION AND IMAGING OF FLUORESCENT ARRAYS

(75) Inventors: Jean I. Montagu, Brookline, MA (US); Stephen D. Fantone, Lynnfield, MA (US)

(73) Assignee: Decision Biomarkers, Inc., Waltham, MA (US)

( * ) Notice: Subject to any disclaimer, the term of this patent is extended or adjusted under 35 U.S.C. 154(b) by 244 days.

(21) Appl. No.: 10/618,838

(22) Filed: Jul. 14, 2003

(65) Prior Publication Data

US 2005/0017191 A1 Jan. 27, 2005

(51) Int. Cl.
*G01N 21/01* (2006.01)
*G01N 21/55* (2006.01)

(52) U.S. Cl. .................. 356/244; 356/445
(58) Field of Classification Search .......... None
See application file for complete search history.

(56) References Cited

U.S. PATENT DOCUMENTS

| | | | |
|---|---|---|---|
| 4,649,280 A | | 3/1987 | Holland et al. |
| 4,857,273 A | | 8/1989 | Stewart |
| RE33,581 E | * | 4/1991 | Nicoli et al. ............. 435/7.2 |
| 5,166,515 A | | 11/1992 | Attridge |
| 5,341,215 A | | 8/1994 | Seher |

(Continued)

FOREIGN PATENT DOCUMENTS

| | | |
|---|---|---|
| EP | 0 575 132 | 12/1993 |
| WO | WO 90/06503 | 6/1990 |
| WO | WO 01/34846 | 5/2001 |
| WO | WO 01/59503 | 8/2001 |

OTHER PUBLICATIONS

Dübendorfer et al., "Reference and Sensing Pads for Integrated optical Immunosensors", *SPIE*, 2928:90-97(1990).

(Continued)

*Primary Examiner*—Michael P. Stafira
(74) *Attorney, Agent, or Firm*—Fish & Richardson P.C.

(57) ABSTRACT

A support for an array of fluorescently labeled samples comprises a transparent body defining:
(a) an array-support surface and (b) under the support surface, in spaced apart relationship thereto, a field of embedded optical features exposed to be illuminated by a broad light beam of excitation radiation addressed to the support from a predetermined general direction selected to produce a surface wave effect at the support surface, the field of embedded optical features and the support being so constructed that light of the beam incident on the features is launched through the support at an angle to the support surface that produces the surface wave effect of radiation in the manner that it can produce fluorescence from the labeled samples to be imaged beyond the support from a direction different from the direction of the illumination. Fine transmissive and reflective features having surfaces generally normal to radiation substantially at the critical angle, and a grating illuminated at a non-normal surface are shown. A data acquision system employing an elastic rotary motion reducer driven by a stepper motor, under computer control, directs a broad illumination beam through a series of small angular increments, an image is taken at each increment by a CCD camera, and based upon energy references on the array-support surface, a quilt image is formed, based on responses of the energy references associated with localized regions of each image.

60 Claims, 25 Drawing Sheets

U.S. PATENT DOCUMENTS

| | | |
|---|---|---|
| 5,344,784 A | 9/1994 | Attridge |
| 5,351,127 A | 9/1994 | King et al. |
| 5,437,840 A | 8/1995 | King et al. |
| 5,486,452 A | 1/1996 | Gordon et al. |
| 5,629,213 A | 5/1997 | Kornguth et al. |
| 5,631,170 A | 5/1997 | Attridge |
| 5,633,724 A | 5/1997 | King et al. |
| 5,666,197 A | 9/1997 | Guerra |
| 5,754,514 A | 5/1998 | Guerra |
| 5,776,785 A | 7/1998 | Lin et al. |
| 5,822,472 A | 10/1998 | Danielzik et al. |
| 5,830,766 A | 11/1998 | Attridge et al. |
| 5,910,940 A | 6/1999 | Guerra |
| 5,945,334 A | 8/1999 | Besemer et al. |
| 6,078,705 A | 6/2000 | Neuschäfer et al. |
| 6,161,437 A | 12/2000 | Brennan et al. |
| 6,255,642 B1 | 7/2001 | Cragg et al. |
| 6,268,125 B1 | 7/2001 | Perkins |
| 6,289,144 B1 | 9/2001 | Neuschäfer et al. |
| 6,356,676 B1 * | 3/2002 | Herron et al. ............... 385/12 |
| 6,362,004 B1 | 3/2002 | Noblett |
| 6,469,755 B1 * | 10/2002 | Adachi et al. ............... 349/62 |
| 6,579,721 B1 | 6/2003 | Natan et al. |
| 6,579,726 B1 | 6/2003 | Natan et al. |
| 6,692,974 B1 | 2/2004 | Perkins |
| 2002/0018199 A1 | 2/2002 | Blumenfeld et al. |
| 2002/0021443 A1 | 2/2002 | Venkatasubbarao et al. |
| 2003/0129654 A1 * | 7/2003 | Ravkin et al. ............... 435/7.1 |
| 2003/0151735 A1 | 8/2003 | Blumenfeld et al. |
| 2003/0223059 A1 * | 12/2003 | Li ............... 356/317 |

OTHER PUBLICATIONS

Dunphy et al., "New planar waveguide attenuated total reflectance techniques for organic thin film spectroscopy and chemical sensing", *SPIE*, 3602:140-148 (1999).

Duveneck et al., "A Novel Generation of Luminescence-based Biosensors: Single-Mode Planar Waveguide Sensors", *SPIE*, 2928:98-109 (1998).

Duveneck et al., "Review on Fluorescence-Based Planar Waveguide Biosensors", *SPIE*, 3858:59-71 (1999).

Enderlein et al., "Comparison between a conventional epifluorescence microscope and a new highly efficient evanescent wave detector in single molecule spectroscopic applications", *SPIE*, 3602:94-101 (1999).

Harrick N. J., "A Thin Film Optical Cavity to Induce Absorption or Thermal Emission", *Applied Optics*, 9:2111-2114 (1970).

Harrick N. J., "Multiple Internal Reflection Fluorescence Spectrometry", *Analytical Chemistry*, 45:687-691 (1973).

"Modern Techniques in Applied Molecular Spectroscopy", Edited by Francis M. Mirabella, *Equistar Chemicals, LP*, pp. 146-147 (1998).

Pinkel et al., "High resolution analysis of DNA copy number variation using comparative genomic hybridization to microarrays", *Nature Genetics*, 20:207-211 (1998).

Silk, Ely, "LED Fluorescence Microscopy in Theory and Practice", *Microscope*, 50:101-118 (2002).

Wittrup et al., "Fluorescence Array Detector for Large-Field Quantitative Fluorescence Cytometry", *Cytometry*, 16:206-213 (1994).

* cited by examiner

Selection of Region of Maximum Signal as Angle $\theta_n$ Changes to $\theta_{n+4}$

EXCITATION AND IMAGING OF FLUORESCENT ARRAYS

TECHNICAL FIELD

This invention relates to the field of microscopic imaging of large fields of view. The invention provides optical systems and methods for high speed imaging of arrays of samples containing fluorescently labeled material, e.g. biologic polymer sequences such as protein, nucleic acid and oligonucleotide arrays, and other fluorescently labeled materials.

The aim of the present invention is to achieve improved performance versus cost of such imaging systems. In general, in low-cost implementations of the invention, it is foreseen that the invention will enable clinical and diagnostic uses that have not previously been regarded as practical economically. Similarly, it is foreseen that lower order educational and investigative uses will be enabled by the invention. The invention is also foreseen to provide higher quality data and better performance in a number of respects than presently possible with available commercial equipment.

According to one aspect of the invention, a versatile, disposable support is provided having fine embedded optical features (microelements) located under the array of fluorescently-labeled samples. By illuminating the field of these features with a broad beam at one or a series of selected angles, the support plays an important role in the lowered cost and accurate functioning of the overall fluorescence excitation and imaging system.

According to another aspect of the invention, novel illumination, imaging and data acquisition techniques are provided that can accommodate variations in the optical characteristics of low-cost disposable supports over their broad surfaces so that data of high accuracy is obtainable despite the low-cost of the system and its disposable components.

Numerous other features of the invention that will be described contribute to achieving these overall goals.

BACKGROUND

Because the conversion efficiency of fluorophores is extremely low, fluorescence microscopy is an extremely inefficient process in which light source-to-detector efficiency may be in the range of parts or a fraction of a part per billion. Another limitation of fluorescence imaging is that the intensity of an illumination source needs to be limited to avoid destruction of the sample or so-called "photo bleaching" in which the capability of the fluorophores to fluoresce is diminished; even before the condition of photo bleaching is reached, the behavior of most fluorophores becomes significantly non-linear or unpredictable, imposing further optical constraints. Numerous non-optical constraints also affect the practicality of the fluorescent microscope design, such as the acceptable duration of a scan of an array, the reliability of the data, the cost of the biochip, the processing complexity and the cost of the scanner.

The state of the art of fluorescence biochip imaging has accordingly been guided by the necessity for a microscope reader to have a very efficient fluorescence-emitted light capture capability. As well, a very shallow depth of field has been important so that only the very thin layer of biological material is imaged, to avoid optical noise perturbations that may be emitted from the support member under the array. This approach has lead to complex and expensive systems: epi-fluorescent scanning confocal microscope readers and cooled CCD camera-based readers that have a small field of view and require moving or tilting with respect to two axes to scan the array.

Some epi-fluorescent confocal or near confocal scanning microscopes employ high precision radiation-directing systems driven by galvanometers or motors and single point detectors such as PMTs or diodes. The text edited by Mark Schena and published by Bio Techniques Books, Natick, Mass. pp. 53–64 carries a summary description of a number of such commercial instruments. Others are also described in U.S. Pat. No. 3,013,467 (Minsky); U.S. Pat. No. 5,459,325 (Hueton); U.S. Pat. No. 5,981,956 (Stern); U.S. Pat. No. 5,895,915 (DeWeerd); U.S. Pat. No. 5,585,639 (Dorsel); U.S. Pat. No. 5,646,411 (Kain); U.S. Pat. No. 5,672,880 (Kain); U.S. Pat. Nos. 6,335,824; 6,201,639 and 6,185,030 (Overbeck).

Examples of fluorescence microscopes that use a CCD array imager as a detector are shown in the Handbook of Biological Confocal Microscopy edited by James Pawley, Plenum Press, 1989 and 1995. Others can be found in U.S. Pat. No. 5,900,949 (Sampas).

In total, the low efficiency of the fluorescent conversion and the other factors mentioned have lead to slow and costly reading of conventional biochips whether by high accuracy scanning of the confocal microscope or by the high cost system of a cooled CCD-based camera associated with a high accuracy scanning mechanism. Such expensive systems have mainly been employed in academic studies and in large efforts directed to drug discovery. No practical way has emerged to enable the technology to be adapted to much lower cost uses such as in medical clinics and diagnostic laboratories, in veterinary medicine, in dealing with agricultural crop diseases and food and water processing, and in lower level educational and investigational laboratories.

An object of the invention is to provide an improved fluorescence imaging approach, and in particular a diagnostic tool that is low-cost and highly effective, useful in direct patient diagnosis and treatment in medicine, as well as for other purposes such as those mentioned.

The invention employs surface light effects to concentrate the illumination in the vicinity of the plane of the sample array. In this way the excitation energy density can be enhanced at the surface of the sample relative to objects at other depths, and imaging can be done without requiring that the imaging system, itself, have a very shallow depth of field. Numerous patents exemplify application of this general technology to experimental microscopy. Examples are U.S. Pat. Nos. 5,633,724; 5,351,127 and 5,437,840 (King) and U.S. Pat. No. 5,341,215 (Seher) and European Patent Application 93304605.4 (EP 0575 132 A1) (King) as well as trade journal articles such as Photonics Spectra, February 2000, pages 24–26. The technique has been described in the Conference on Advances in Fluorescence Sensing Technology IV, 1999, Vol. 3602 pp. 140–148 and pp. 94–101; the Proceedings of SPIE Vol. 4252 pp. 36–46, SPIE Vol. 2928 pp. 90–109 and SPIE Vol. 3858 pp. 59–71, and the book Internal Reflection Spectroscopy by F. M. Mirabella Jr. and N. J. Herrick. See also U.S. Pat. Nos. 5,910,940, 5,754,514 and 5,666,197 (Guerra) and U.S. Pat. No. 6,078,705 (Neuschafer et al.), from different fields.

The potential of surface wave techniques for illuminating and detecting specific binding analytes is also well documented. A number of the techniques proposed use prisms or gratings to induce evanescent fields. Other related techniques such as Surface Plasmon Resonance (SPR) couple evanescent incident radiation into a mode generated between a thin metal layer, such as gold or silver, and a dielectric layer such as silicon or phosphate glasses or silane. Such techniques have been described in U.S. Pat. Nos. 5,830,766 and 5,631,170 and PCT WO90/06503 (Attridge).

A preferred technique to create an evanescence fluorescence-enhancing surface wave described in certain of the above references is to illuminate the substrate at a defined illumination region, via an intermediate support. The light arrives at the surface at a suitable angle to induce an evanescent wave on the surface. To excite the sample, the energy then travels laterally along the surface to a separately defined sample region where the sample is excited. Often a large 90 degree prism member has been employed which is coupled to a separate member carrying the biology. Varying the angle of the incident light permits the accommodation of a range of illumination wavelengths. A conventional microscope has then been used to inspect the fluorescence. By this technique, illumination of the sample has been enhanced without the penalty of incident light being reflected into the objective of the reader. Often a fluid coupling agent between the mated optical parts is required. A variation on this technique has used a grating at an illumination region separate from the imaging region, and the angle of illumination of the grating has been tuned to maximize the signal, see Review on Fluorescence-Based Planar Wave Guide Biosensors, Duveneck et al., Vol. 3858, 1999. In another field a large transparent optical block has been employed to couple light to a sample at various angles for sectioning the sample at various levels, see e.g. U.S. Pat. No. 6,255,642 (Cragg et al.)

Applications exist where such previously designed surface wave systems may be justified, but these designs have not proven suitable for low-cost clinical usage and the like.

One previously proposed substrate for imaging a fluorescing array has been a microscope slide having an interference grating buried under a thin layer of high index glass. In that example the grating was arranged to reflect normal incident light that has not been absorbed by the sample (a very large fraction) at a suitable angle to induce an evanescent wave at the sample. The intensity of the evanescent wave can be more than an order of magnitude greater than that of the original incident light beam, but, because gratings reflect normal incidence beams at different angles for different wavelengths, to operate beneficially, each slide was generally restricted to its design wavelength.

U.S. patents disclosing other use of gratings include U.S. Pat. No. 5,822,472 (Danieizik et al.) and U.S. Pat. Nos. 6,078,705 and 6,289,144 (Neuschafer et al.) In these and in other cases the array to be imaged has been incorporated in a flow cell arrangement, see also for example U.S. Pat. Nos. 5,166,515; 5,344,784; 5,631,170 and 5,830,766 (Attridge); and U.S. Pat. No. 4,857,273 (Stewart).

Prior art CCD-based, fluorescent, conventional or confocal scanning microscope systems can provide high quality images of material located on the top surface of a support. But in their compromise between depth of field, energy collection efficiency, laser power, damaging of the sample by photo bleaching, capture time requirements and cost and the precision and complexity associated with establishing evanescence light concentration, high cost of the support, uncertainties caused by operating in a non-linear region of the fluorophores, etc., they have not been altogether satisfactory.

It is well known that evanescent illumination of a biochip has had the potential to offer a much higher signal than conventional illumination, such that a CCD-based imaging system can be used to acquire the image information on the biochip without loss of data. The apparent requirements and cost of prior proposals to reliably induce evanescence, however, has apparently impeded commercialization of the techniques.

The present invention provides low-cost, robust and wave-length versatile systems and techniques incorporating surface wave technology that are foreseen to enable a breakthrough in the technology.

SUMMARY

According to the invention, illumination of a broad surface of a biochip substrate is employed to illuminate a large array of spots of the biological material. A pattern of fine embedded optical features (microelements) disposed over a broad surface of the transparent, array-carrying substrate, beneath the array, intercepts the incoming broad beam of illumination traveling at a selectable angle and enables the illumination to travel through the substrate at an appropriate angle to the surface carrying the array of samples to establish an evanescent wave or other surface wave illuminating effect that concentrates the illumination energy substantially at the plane of the array of biological samples.

The present invention also provides novel systems, methods and apparatus for accepting and employing the novel disposable biochip for high accuracy imaging of large regions on the biochip. In particular, the invention provides for obtaining an image at a selectable wave length of thin material of organic or inorganic nature on the support surface at high resolution, high sensitivity and high speed.

The function of the fine embedded optical features of the array support is to efficiently assist the launching of the excitation beam at the suitable angle so as to stimulate the excitation of the fluorophores on the broad surface of the support that lies opposite the embedded features, without causing equivalent emission in the base support material that would create optical noise perturbation. Since they are embedded in the supporting substrate, the embedded optical features do not necessitate coupling of one member to a discretely separate biochip or substrate member. A simple wide field of view CCD-based camera can be used with this system to obtain equivalent information to that which has been obtainable from more expensive commercial systems; or, by employing a more complex CCD camera or scanning microscope principles, superior image information can be obtained, according to the invention.

In one aspect of the invention, embedded optical features of the sample support are simple, shallow transmissive or reflective formations that enable the illumination of the sample and reduce performance requirements of the microscope.

Another aspect of the invention is the provision of a cassette or flow cell that incorporates the described array support within a reaction chamber suitable for further processing in an automated or semi-automated protected environment.

Important features of the design include computer-controlled variation of the angle of approach of the illumination beam to the biochip, and dynamic varying of that angle by steps over a range, taking a full wide image at each step, and processing that data in manner that optimizes the signal obtained for localized portions of the biological array being imaged, to provide a composite or quilted image of localized best results.

Another aspect of the invention is a system which controls incident illumination to optimize surface stimulation and fluorescence emission, that involves both sequential illumination of the array in steps over a range of incident angles and novel protocols for selecting the results from the optimum angle for localized regions of the array based on energy references strategically located with respective localized regions of the array on the disposable biochip or substrate.

In the present invention, because of the high level of excitation at the plane of the sample, a camera with a large depth of field is employed, e.g. a CCD camera, and because the time required to take a complete image of the wide area may be of the order of one second, the very small fraction of a second required to index from one angle of illumination to the next for another full image is negligible; likewise the overall time to take full images in steps over a range of 10 or even 20 adjacent angular increments and to process the information for optimizing the reading for each local portion of the imaged array, according to the invention, is readily affordable.

A particular aspect of the invention is a fluorescence reader, preferably a CCD-based imager or camera, capable of broadly illuminating and acquiring a wide field of view image of the sample. One feature of the reader is a system that provides a variable angle of incidence, broad illuminating light beam constructed with suitable range and resolution that compensates for the variation of the critical angle encountered with a wide range of different biological products deposited on the biochip as well as variations due to manufacturing tolerances in the geometry of the disposable biochip and variations of the index of refraction of its base material.

Another aspect of the invention is the use of quasi-collimated light, i.e. light that is slightly divergent or convergent, i.e. divergent or convergent over an angular range of no more than about 5 degrees, preferably less than about 2 degrees. At the cost of somewhat less efficient use of the light, the angular spread helps to ensure that at least some of the light reaches the array surface at the angle required for producing a desired surface effect in the presence of localized imperfections or misalignments. In conjunction with use of quasi-collimated light, it is advantageous to employ a low-cost L.E.D. chip having an X-Y array of light-emitting diodes as an inexpensive, slightly divergent light source for a low-cost version of the instrument, in lieu of use of a laser light source.

In such ways as described above, a simple, low-cost sensor platform, i.e. a broadly illuminated biochip substrate itself, is able, at various selectable wave lengths, to induce luminous excitation for fluorescently exciting a broad array of biological material deposited, spotted or otherwise provided on the substrate. This disposable biochip and its microscope reader cooperate to optimize consistent and reproducible imaged information within practical commercial manufacturing tolerances.

In preferred embodiments, for producing stepped motion of a broad beam-reflecting mirror for taking a succession of images of the fluorescing array at angular increments, an elastic motion divider is employed in which a motor, preferably a stepper motor, deforms a weak spring attached to a stronger spring of a similar nature anchored rigidly at the other end. The motion at the interface between the weak and stronger springs is approximately proportional to the ratio of the rigidity of the two springs, and is the location where the mirror for stepping the angle of the beam is mounted. Preferably the springs are torsion springs driven by a rotary stepper motor. In certain embodiments two such motion reducers are mounted in cascade to achieve a two axis mirror motion. Damping of settling motions is advantageously employable to increase the operating speed of the system.

While this elastic motion reducer is presently preferred for its simplicity and characteristcs, the tilt mirror (or the tilting of the support) can for instance be controlled by other known precision mechanisms, for instance galvanometers, gear-reduced stepper motors DC motors with encoders, and any other suitable motors with motion reduction mechanisms.

Selection of best localized regions from a set of images taken at adjacent angles based on energy references, for forming a quilt or tapestry composite image is preferred. In certain cases, two or more images, or two or more localized images from respective regions, may be added to obtain an image, or localized region image for a tapestry, having improved signal to noise ratio.

While the image acquisition methods proposed here are preferably applicable to wide field of view, two-dimensional CCD-based microscope systems, the unique disposable biochip substrate can also be used with a one dimensional CCD-based microscope with single direction scanning or with conventional fluorescence microscopes, confocal microscopes or flying spot scanning microscope systems.

The fine embedded optical features that assist in launching the light to the top surface are defined such as to cooperate with the angle of the generally collimated, wide beam incident on the support. The periodic pattern of the embedded optical features as well as the array-receiving area of the substrate can extend over the dimension of the field of view of the reading instrument and is selected in accordance with the dimension of the spots or other features of interest of the material to be inspected, as well as in accordance with the angle of incidence of the excitation beam. By suitably fine dimensions of the embedded optical features, the obscuration associated with the edges of the optical features is caused to limit artifacts to those that are small in effect on the response with respect to the response over the full dimension of the spots of the inspected sample. Preferably, to avoid detrimental or non-uniform artifact effects by the edges of the optical features, the period of the features is selected to be in the range between about ¼ to ⅟50 of the size of the sample spots, preferably of the order of ⅟10 the dimension of the smallest sample spot size to be employed on the respective substrate.

For the range of biological spot sizes between 50 and 500 micron diameter, a periodicity of the embedded optical features is preferably between about 1 and 50 micron.

For providing the embedded optical features the invention in particular includes the support formed with triangular shaped grooves at a suitable angle in transmissive or reflective geometry such that the light moves from the facets of the grooves through the transparent body of the support at the critical or other appropriate angle to the top surface of the support. In certain preferred embodiments the features are at the bottom surface of the support and are protected, for handling purposes, with a layer of organic or inorganic material.

According to a further aspect of the invention, the sample support with the embedded optical features is constructed as a substrate similar in size and shape to a conventional microscope slide. This provides a disposable substrate that, in size and shape, is entirely familiar to clinical laboratory personnel and the like, and suitable to be handled and spotted by robotic equipment that already exists in laboratories or clinics. In some preferred instances, the top surface of the sample support receives the sample to be imaged and the bottom surface is shaped to transmit light to the top surface such as to cause an evanescent wave or to induce another surface-concentrating effect to the light energy at that surface, to concentrate illumination energy at the plane of the array. For producing such effect, the excitation light enters the bottom surface, e.g. via facets of the embedded optical features, at an angle approximately normal to the critical angle which is defined by the top surface of the substrate, the material of the biochip and the biological medium/air interface. By approaching with approximately normal incidence, detrimental refraction effect by the body of the support is avoided.

According to another aspect of the invention, the sample support having the embedded optical features is likewise built in the form a substrate similar in size and shape to a conventional microscope slide, the top surface which receives the sample to be imaged is coated with single or multiple layers in manner to create wave guide conditions adjacent the top surface, and the bottom surface is shaped to transmit light to the top surface such as to cause light energy to concentrate in that wave guide along the top surface. The excitation light again may enter the bottom surface, e.g. via facets of the embedded optical features, approximately normal to the appropriate angle for entering the wave guide, defined by the top surface, the material of the biochip and the biological medium/air interface on it.

For such transmissive embedded optical features, the invention in particular includes the bottom of the support formed as triangular shaped grooves at a suitable angle such that light incident upon the features from outside is transmitted through the transparent body of the support at the critical angle to the top surface of the support. In certain preferred embodiments that surface is protected, for handling purposes, with a layer of organic or inorganic material.

In another aspect of the invention, the sample support having the embedded optical features is also preferably built in the form of a transparent substrate similar in size and shape to that of a conventional microscope slide, and the top surface receives the sample to be imaged. In this case, the broad top surface bearing the sample array is adapted to receive the excitation light from above e.g. at an approximately 45-degree angle of incidence to the top surface. The bottom surface is shaped to define fine reflective features and is coated to reflect that light which enters the substrate from the top and is not absorbed or deflected by the sample being inspected. Due to the orientation of such fine reflective features, the reflected light is directed back toward the top surface at the desired angle, e.g. the critical angle that creates a surface wave effect, such as an evanescent wave along the top surface. By suitable orientation of the fine reflective surfaces relative to the predetermined location of the illuminating source, substantially no light is directed back into the source, nor is it directed into the imager.

For such reflective embedded optical features, the invention includes the bottom of the support formed as triangular shaped grooves having walls disposed at suitable angles and coated with a reflective material such as aluminum, silver or gold, for suitably internally reflecting incoming light from the top, to be redirected at the critical angle to the top surface. In certain preferred embodiments that reflective surface is protected for handling purposes with a layer of organic or inorganic material.

In order to create a surface wave at the top of a substrate, the light must travel through the substrate to the surface at an angle (the critical angle) defined by the index of refraction of the substrate. If the substrate is polycarbonate or polystyrene with an index of about 1.59 and the sample on the top surface has an index of refraction of 1 (equal to that of air) the critical angle is approximately 38.9 degrees to the normal. The choice of substrate material (e.g. polystyrene) and the index of refraction of the sample defines the angle of incidence with the normal to the surface. For most common biological sample materials the critical angle is in the range of approximately 30 to 60 degrees, a range of about 30 degrees or 0.5 radian, considering the use of materials having conventional indices of refraction as well as those materials having more extreme indices of refraction, some of which are commercially available while others are to be expected. In many cases the preferred range is from 38 to 44 degrees to the normal, a range of about 6 degrees or 0.1 radian, using materials such as those employed in the preferred embodiments described herein.

In some embodiments of the invention, the top surface of the support is coated with a material of lower index of refraction than that of the support, and in other embodiments it is coated with alternate layers of high and low indices of refraction to create a wave guide condition in which the light is confined as it moves along the surface bearing the array of biological material until it is absorbed by the biological material. In such cases, advantageously according to the invention, the top-most layer over such coating layers is a layer of biology-binding material deposited in solution with a solvent that evaporates such as chloroform or other manner of coating such as by vapor deposition. Polystyrene is a suitable such material to which biological material binds, and there are other known coatings that have the characteristic of both adhering to the selected final coated layer of the support and to the biological material to be deposited.

In still other embodiments of the invention the deposited and dried sample spots themselves are sized and adapted to define Fabry Perot-like resonant cavities for the illuminating radiation that proceeds along the plane of the array, the excited fluorescent radiation being able to escape from the sample because of its differing wavelength. In some cases, to properly adjust the spacer thickness of the Fabry Perot cavity, a coating on the support of special thickness and refractive index matched to the sample cooperates with the thickness of the sample spot to define the thickness of the spacer of the Fabry Perot-like cavity.

In other embodiments of the invention, the bottom surface of the biochip support beneath the area of the support that carries the array of biological sample is formed as a diffraction grating having characteristics such that a broad excitation beam of light with non-normal incidence (e.g., offset at 10 to 15° from normal) is diffracted and directed to the top surface of the support at the critical angle, the camera or other microscopic viewing instrument being arranged with viewing axis normal to the array surface, not being in line with the direction of the angled incident radiation so it does not collect any radiation that may continue along its original path.

The invention also provides unique methods of manufacturing low-cost, versatile, disposable array supports having embedded optical features for evanescently exciting, or otherwise employing surface wave effects, to produce luminescence in proteins, antibodies, antigens or nucleic acids labeled with luminescent dyes, as well as luminescence from other labeled materials.

In various embodiments, the embedded optical features are formed as grooves of shape chosen to optimize the uniformity of the surface wave over the entire region of interest. These optical features range between sub-micrometer dimension and periodicity to as large as a fraction of a millimeter, dependent upon other characteristics of the system, especially the size of the spots in the array as previously mentioned. In some embodiments, according to the invention, to accommodate a range of wavelengths, the index of refraction of the support itself is varied according to location of the region of incidence of the light and the location and dimensions of the spots and array pattern. Also in certain embodiments, with some deviation of the angle of incidence of the illumination, adjacent grooves with slightly different reflection angles are provided in the support or, in these and other cases, a slight curvature may be provided in the optical surfaces, or the light is provided as only quasi-collimated light as mentioned above.

It is characteristic of the invention that the source light is reflected to induce a surface wave at the top surface at a location slightly offset from its precise point of incidence on the substrate, the deviation being approximately equal to the thickness of the substrate. In certain embodiments of the invention, this deviation is minimized by use of a thin substrate mounted on a rigid surrounding support.

An alternate manufacturing method according to the invention is to form desirable reflective embedded optical features on the top surface of a suitably rigid base and deposit a coating of suitable thickness and index of refraction onto that, the upper surface of this coating defining the surface on which the sample to be inspected is placed. The index of refraction of such coating is selected to accommodate the geometry of the reflective features, the index of refraction of the inspected sample and the wavelength of interest. Such coating, and others mentioned herein, can be silicon dioxide, titanium dioxide or other material having an index of refraction suitably higher than that of the inspected sample.

In operation, fluorescently labeled biological material is deposited on the top surface of the support as an array opposite to the field of fine embedded optical features; the excitation beam of broad size preferably arrives at the substrate to illuminate an area larger than the wide-field of view of the reading instrument. The light is directed by the beam deflection mirror in cooperation with the field of fine embedded optical features to produce a surface wave effect by any of the techniques described above. The fluorophores are excited and emit light at their specific emission wavelength, and the emitted energy is collected by the objective of the imager. In preferred implementations of the invention, the excitation light beam is approximately collimated and the inclination of the redirecting mirror is defined to accommodate the incidence of the excitation, and constructed to be adjusted to accommodate possible variations in the instrument and biochip geometric features as well as variations or uniformity variations in the indices of refraction of the material of the support are the biology inspected.

In an alternate implementation, the biochip is designed to accommodate an excitation beam aimed axially with the axis of the reading instrument, and, for instance, the angle of the biochip rather than the angle of the incident illumination may be varied, or both may be varied.

The material of the disposable support may be virgin polystyrene with an index of approximately 1.59 or polymethylmethacrylate (PMMA, known as Plexiglas,™) or polycarbonate or similar plastic having an index of refraction between about 1.49 and 1.59, respectively. The fine optical features may be created in the substrate by forced embossing at proper temperature of the substrate, by being cast or press-formed against a suitably formed negative master in a manner akin to the techniques commonly used to create CD and DVD discs or cast of molten material in a mold. The features may be as small as a fraction of a micron but possibly as large as tens of microns or hundreds of microns, depending upon sample spot size, as noted above. The selected geometry of the embedded optical features, e.g. the angle of the reflecting surface or the periodicity of grating lines is determined by the index of the material of the support and any coating as well as the angle of incidence of the excitation source such as to induce a surface wave, these being dimensions which may be chosen to optimize the manufacturing process selected.

Thus, another aspect of this invention is that microscope slides of standard dimension having the broad field of embedded optical features are made employing technology presently used to manufacture CDs and DVDs, at comparable cost.

Another aspect of the invention is a cassette or flow cell for hybridization incorporating the novel support that has been described. The support with its field of embedded optical features is preferably nested in a cassette having a protective cover, for instance a cover of rigid material having a deformable seal rim or bonded membrane that protects the biological material.

Another aspect of the invention is a system, as described, that achieves an optical efficiency that is more than one order of magnitude greater than that which has been achieved with conventional microscope slides, using, according to the present invention, an imager the complexity of which is greatly reduced from that presently available commercially.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
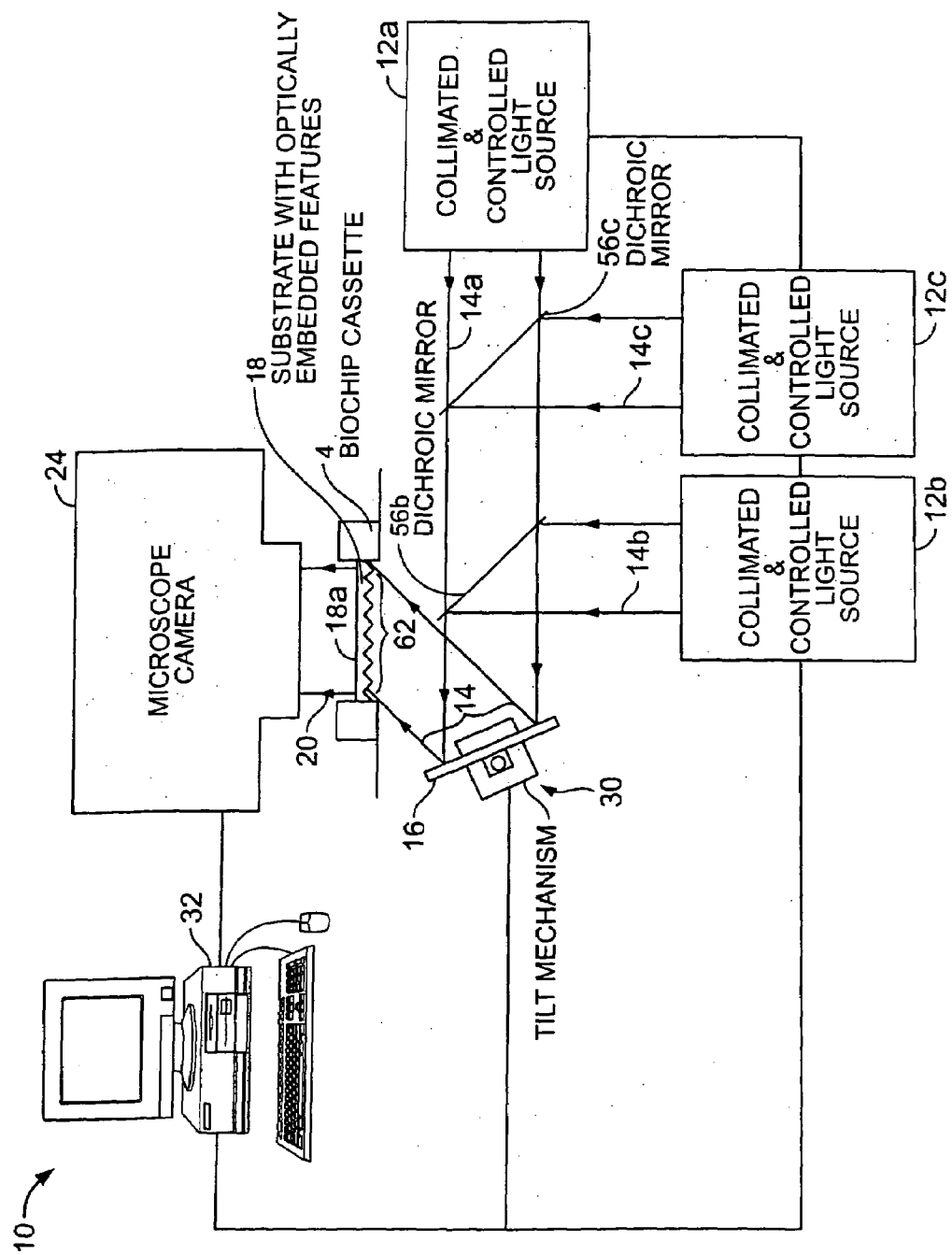
FIG. 1 is a diagrammatic view of an image acquisition microscope according to the invention, having its broad excitation light beam inclined at a controllable angle to illuminate the broad area of a biochip carrying a field of fine embedded optical features under the array support. The arrangement enables transmission illumination such as to create a surface wave to induce fluorescent emission of tagged biological material located on the top surface of the biochip opposite the embedded optical features.
Figure 3:
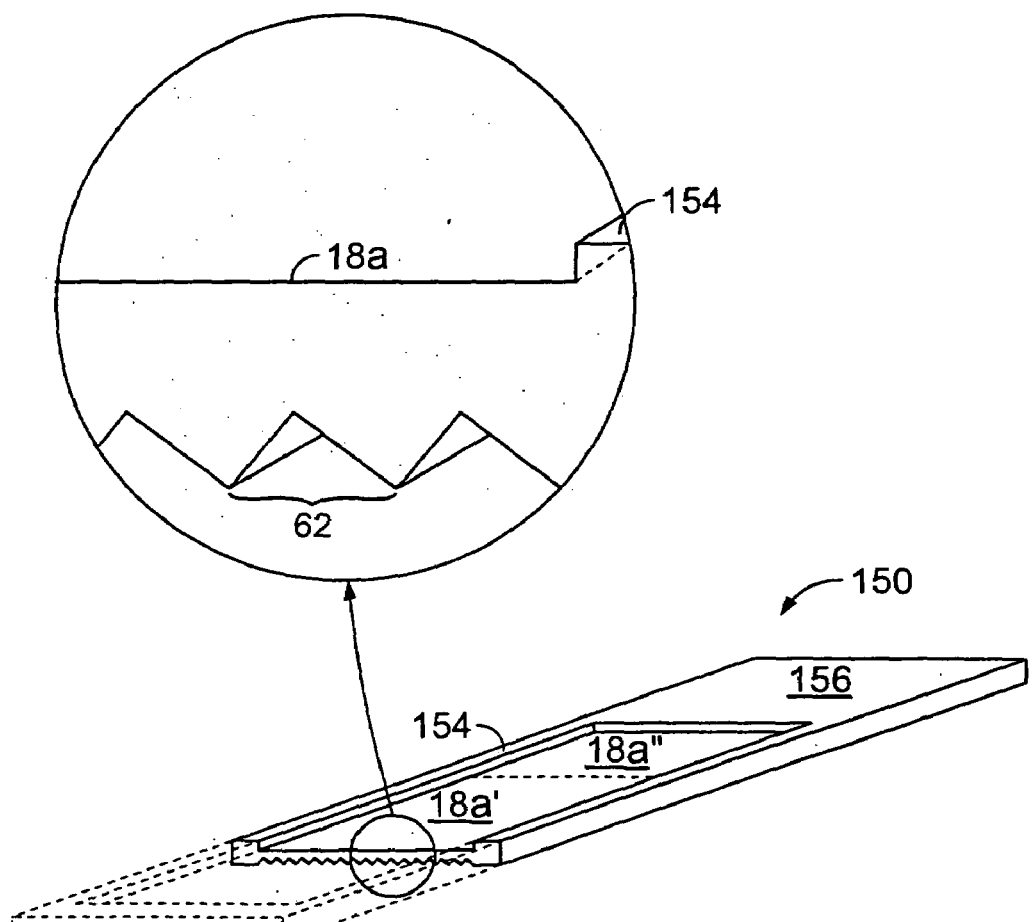
FIG. 3 is a perspective view, including, as indicated, a blow-up of a small portion, of a biochip constructed in the form of a microscope slide, according to the invention.
Figure 3A:
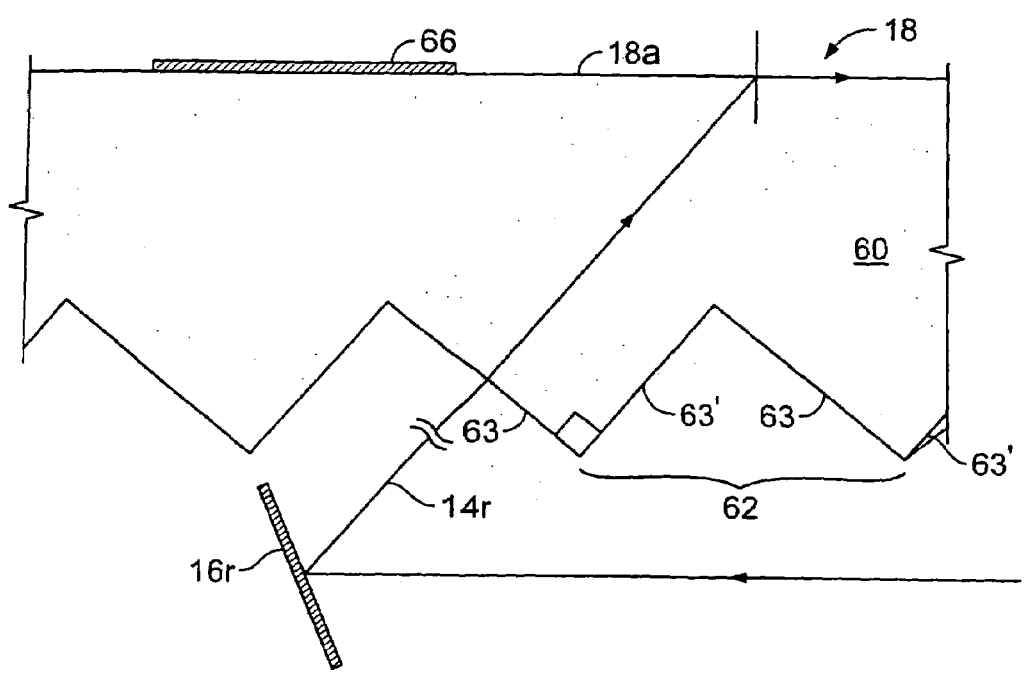
FIG. 3A is a schematic presentation showing, in representative form, the light path striking a biochip built for transmission illumination, employing embedded refractive optical features which stimulate a surface wave to induce fluorescent emission of a tagged area of an array on a biochip.
Figure 3B:
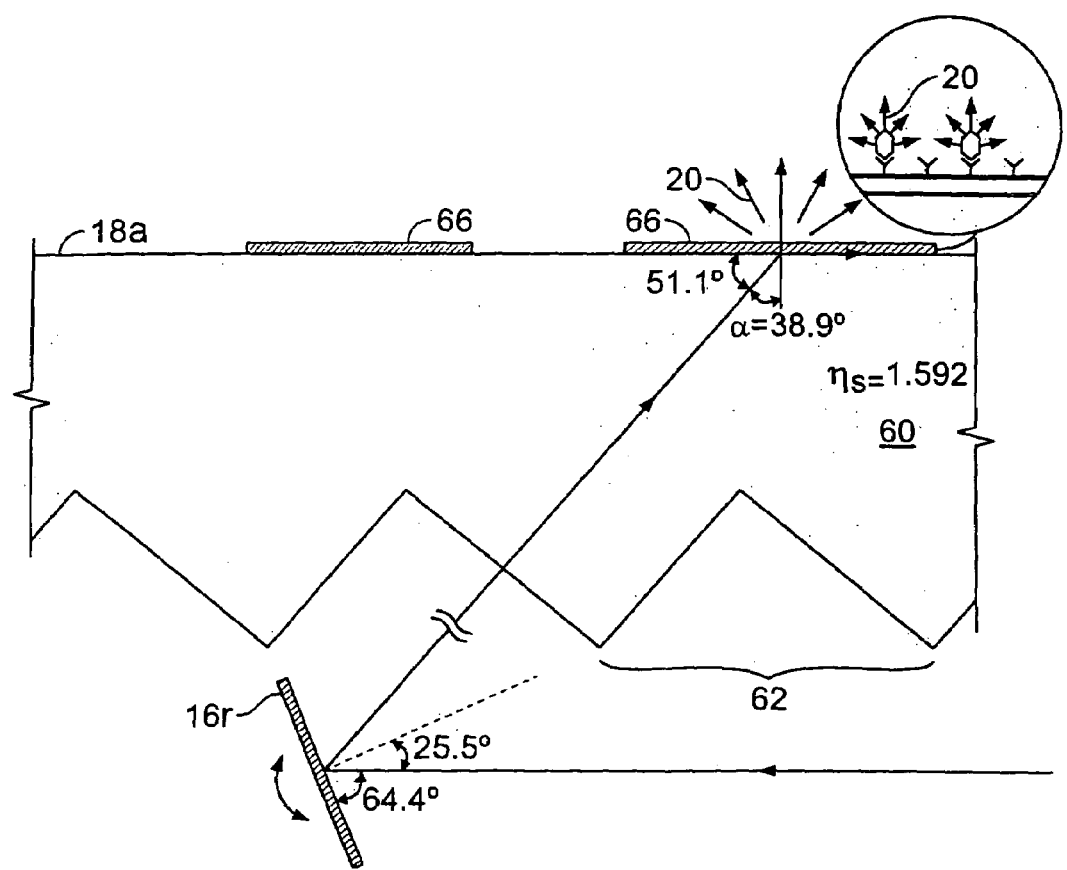
FIG. 3B is a schematic presentation similar to that of FIG. 3A of the same arrangement specific to inducing fluorescent emission of a tagged area employing a substrate of polystyrene having an index of refraction 1.59 and a sample having an index of refraction of 1.0.
Figure 3C:
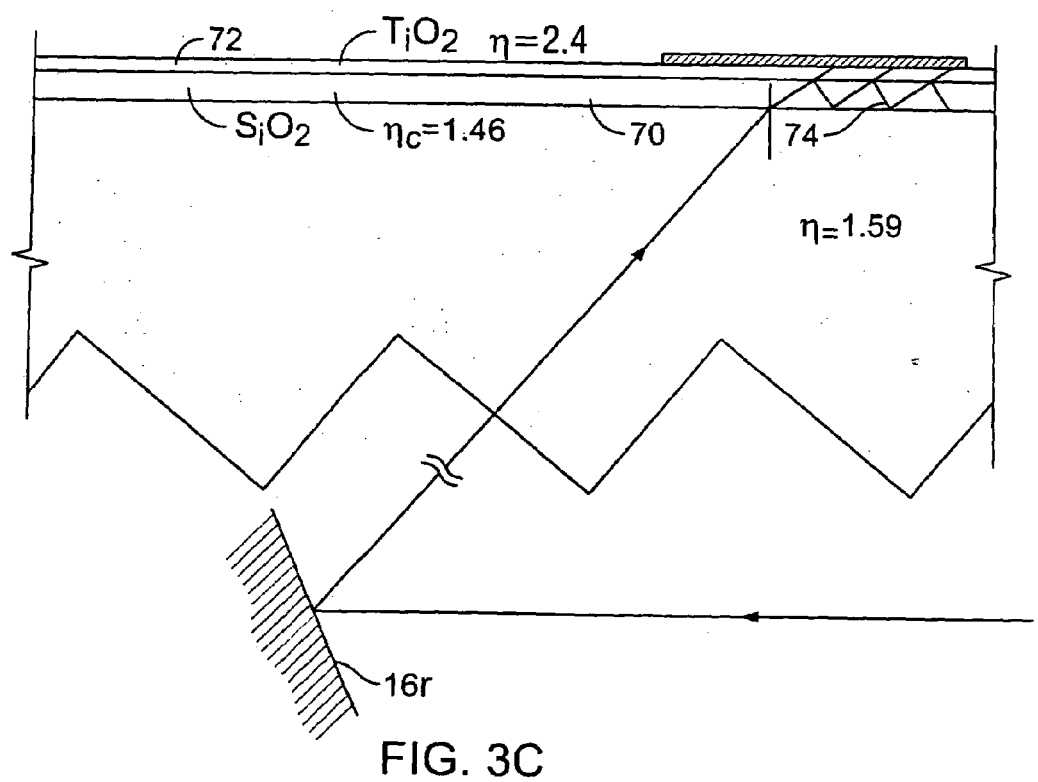
FIG. 3C is a schematic presentation, similar to FIG. 3B, of an embodiment employing a wave guide formed by coating on the top surface.
Figure 3D:
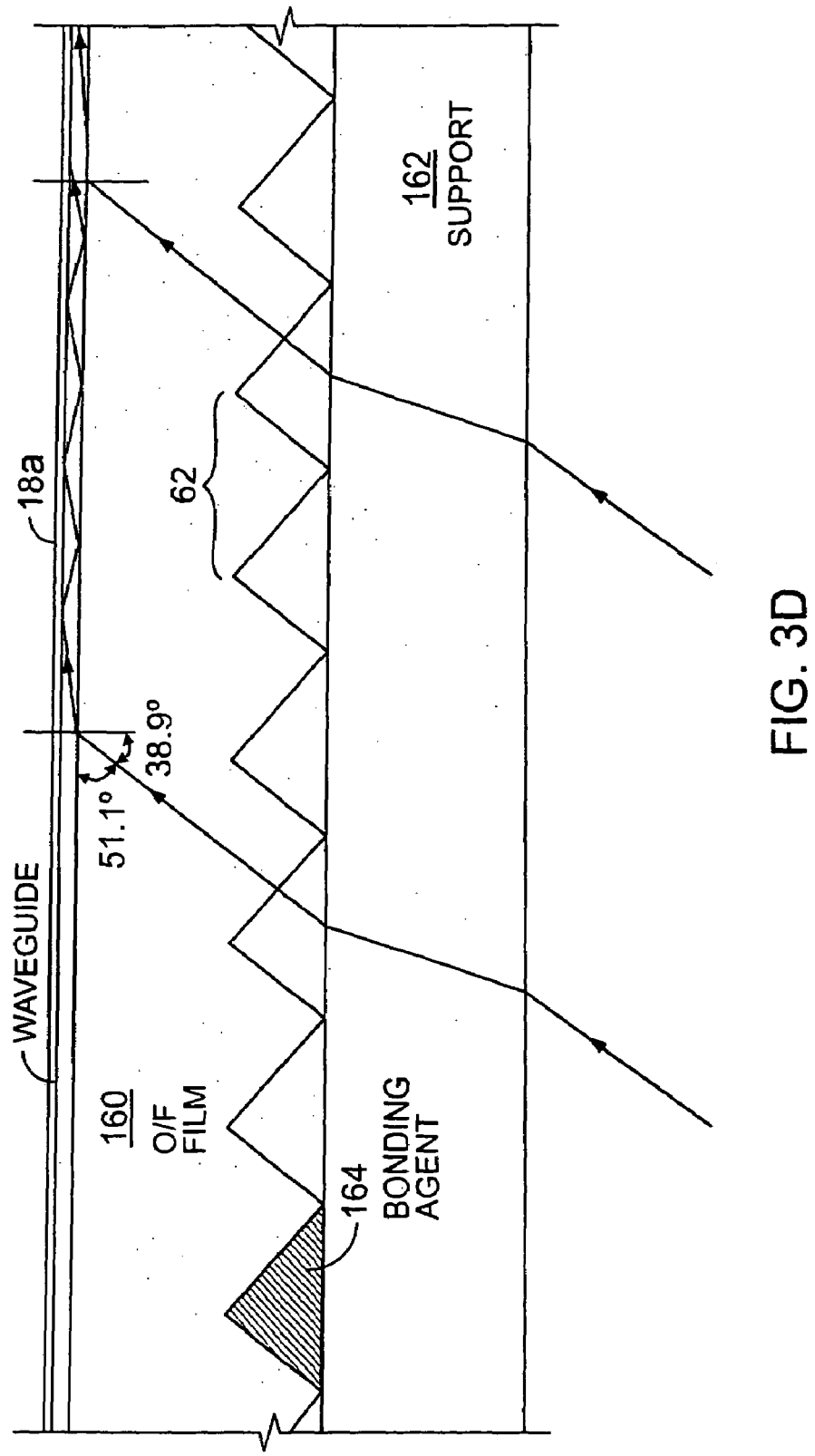
FIG. 3D is a schematic presentation of an alternate construction in which a thin film formed with embedded optical features is bonded to a thicker support.

In the preferred embodiment of FIG. 1 an optical imaging system 10 is provided for examining biological material located on a transparent substrate 18 of a biochip that has a field of fine embedded optical features 62 under the sample receiving surface 118a shown in FIGS. 3–3C or 3D. In the particular embodiment shown, the substrate with the embedded optical features 62 lies directly opposite the array to be imaged. The field of optical features 62 forms an important part of the optical system for increasing the detected optical signal and is described in detail later below.

Optical system 10 includes light sources 12a, 12b, 12c (and others may be added), each equipped with an obscuration device and suitable filters, not shown. These light sources are capable of launching approximately collimated, monochromatic light beams 14a, 14b and 14c, of respectively different selected wavelengths. The beams proceed along the same path, being merged by associated dichroic beam splitters 56b and 56c. The beam is reflected by rotatable mirror 16 controllably stepped by tilt mechanism 60. The reflected light passes into the substrate 18 as a broad excitation beam 14 that is transmitted by the transparent substance of support 18 at the desired angle. At top surface 18a of the support 18, the beam induces a surface effect that stimulates fluorescent emission 20 from the array of biological material on that surface. The emission is imaged by CCD camera 24. Data from camera 24 is transmitted to computer 32 which analyses the data and actuates mirror tilt mechanism 30 to select the angle of illumination for the images. In operation, the computer controls an initiation protocol which includes obtaining anticipated signals from selected fiducial reference spots in known locations on the substrate, e.g. for alignment purposes. Subsequently, the computer program may direct the tilt mechanism 30 to step through a coarsely selected number of angles to optimize the signal coming from known energy reference spots placed on the substrate according to the invention, in order to define a best range of tilt positions for response for each local region of the substrate 18. In the embodiment shown, the mirror tilt mechanism 30 has one axis of motion, while in other embodiments it may have two axes of motion. In a preferred form, the biochip cassette 4 has a rigid perimeter structure that is integral with substrate 18 and is of overall form similar to that of conventional microscope slides, e.g. 25 by 75 mm in width and length and approximately 1 mm thick.

Figure 1A:
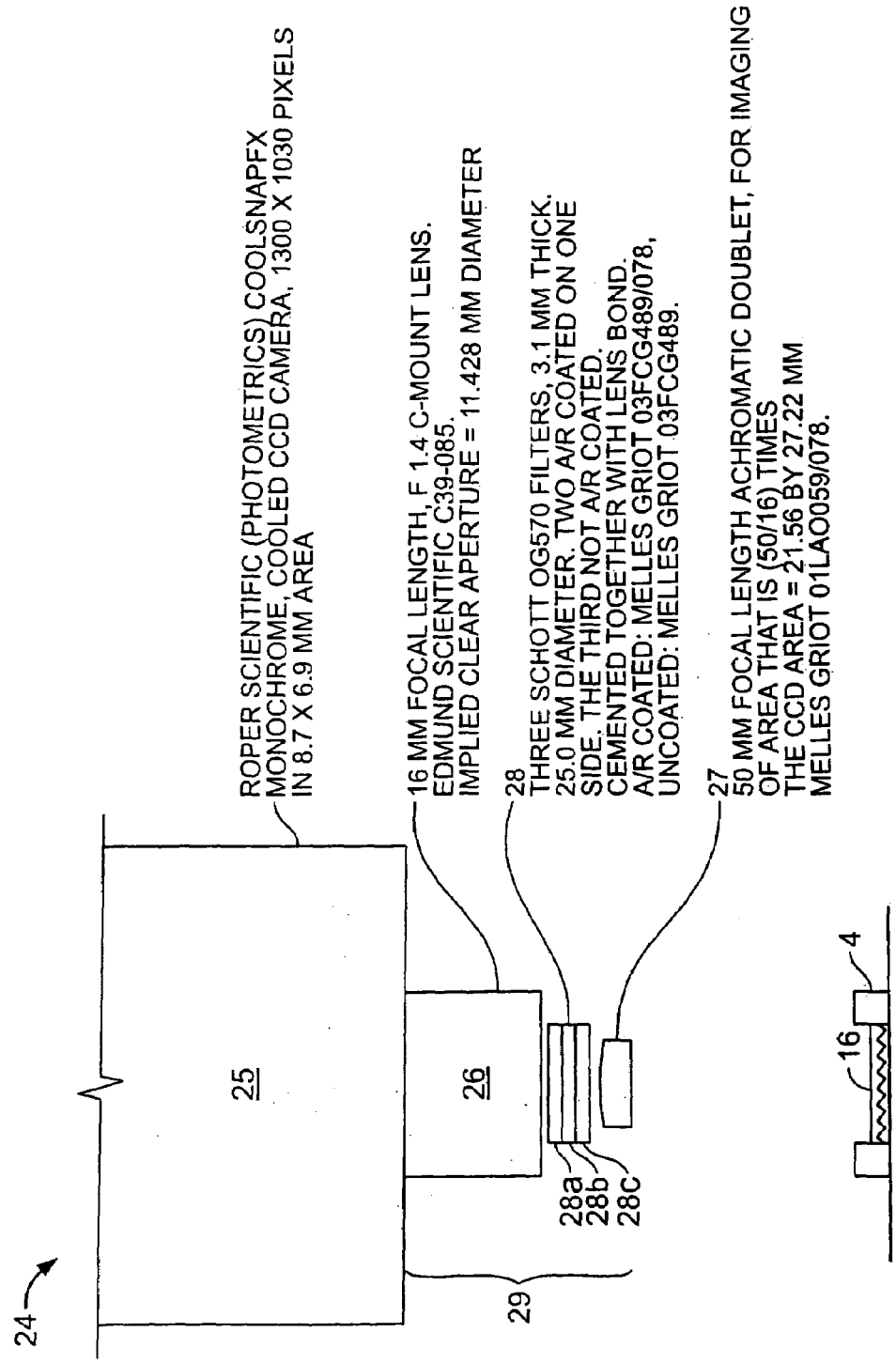
FIG. 1A is a diagrammatic view of the CCD camera of FIG. 1 with its associated lenses and filters.

FIG. 1A illustrates details of the camera system 24. It includes CCD camera 25, which may for instance be a cooled monochrome CCD camera from Roper Scientific, Coolsnapfx. The camera is provided with an objective 29 comprised of lenses 26 and 27. Lens 26 for example may be Edmund Scientific part C39–085, a 16 mm focal length F# 1.4 C-Mount lens and lens 27 may be a 50 mm focal lens achromatic doublet, such as Melles Griot part #01LA0059/078. Narrow band pass filters 28A, 28B and 28C are associated, as needed, for the respective fluorescent tags being used on the biological polymer and the correspondingly associated wavelength of light source 12A, 12B or 12C.

Figure 1B:
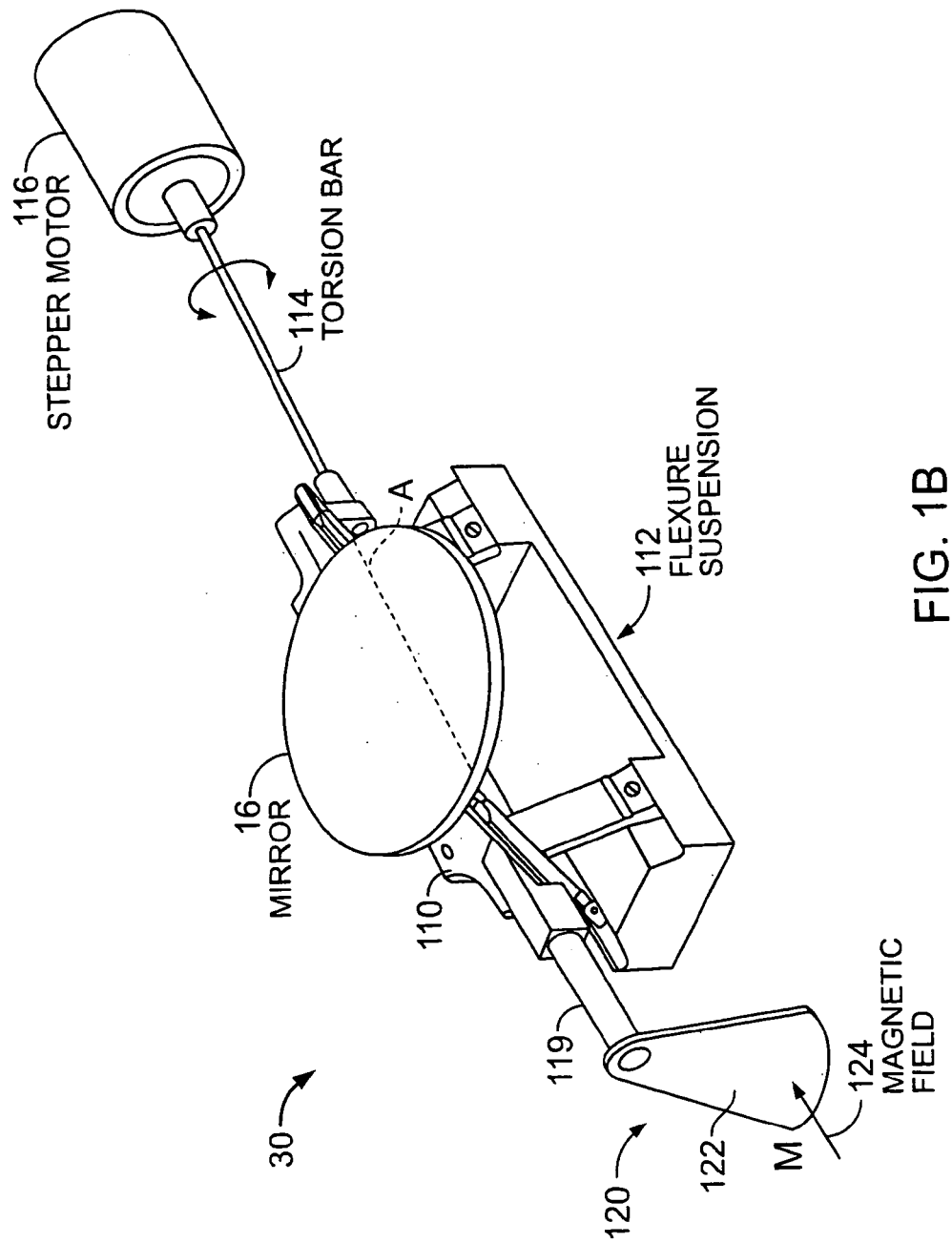
FIG. 1B is a perspective view illustrating a beam-directing mirror mounted on a flexure motion reducer having magnetic damping.

Referring to FIG. 1B, prime mover mechanism 30 rotates mirror 16 with selected small incremental motion. Mirror 16 is mounted on armature 110, supported by relatively rigid flexure suspension 112 acted upon by more flexible torsion bar 114 attached to the shaft of rotary stepper motor 116. Magnetic damper 120 associated with an extension shaft 119 consists of conductive damping blade 122 made preferably of low resistivity material such as aluminum, copper, silver or gold, held within a magnetic field 124 of a permanent magnet structure, not shown. This arrangement tends to magnetically dampen settling movements of the armature 110 in known manner. A reference position indicator may also be associated with damping blade 122. In this construction, mirror 16 is free to rotate about only one axis A and is rigidly held against motion along all other axes. It should be noted that slight linear translation of the mirror in a direction parallel to its surface may result from the torsion system during rotation but this has substantially no effect on the system. The torsional resistance provided by the flexure suspension 112 is selected to be substantially stiffer than the torsional resistance of the torsion bar, such that one rotary step of the stepper motor 116 results in displacement of the mirror by a substantially reduced motion, e.g. $\frac{1}{80}^{th}$ of the step angle.

Figure 1C:
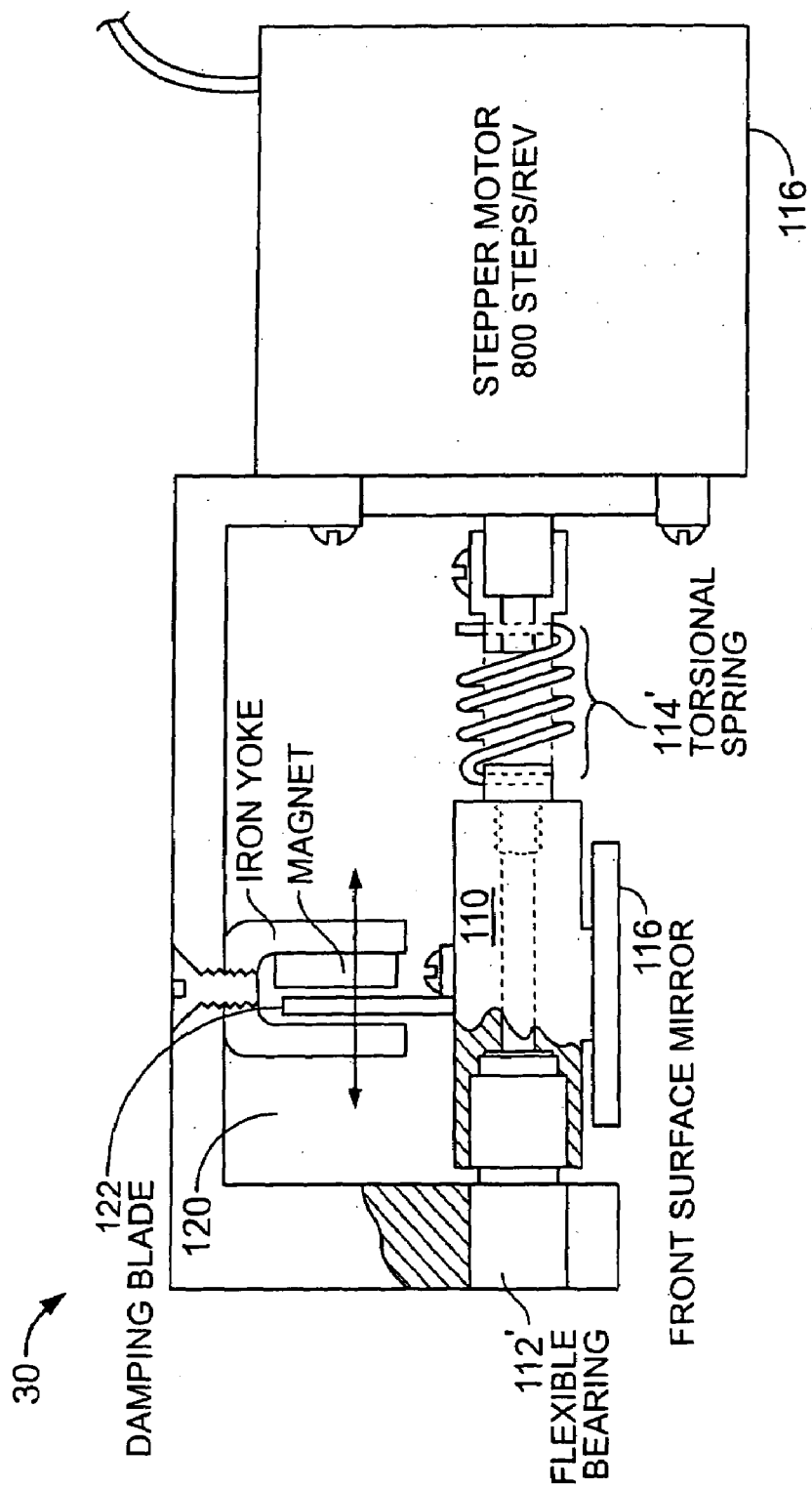
FIG. 1C is a partially broken-away side view and FIG. 1D an end view of a preferred rotary motion reducer that moves a beam-directing mirror.
Figure 1D:
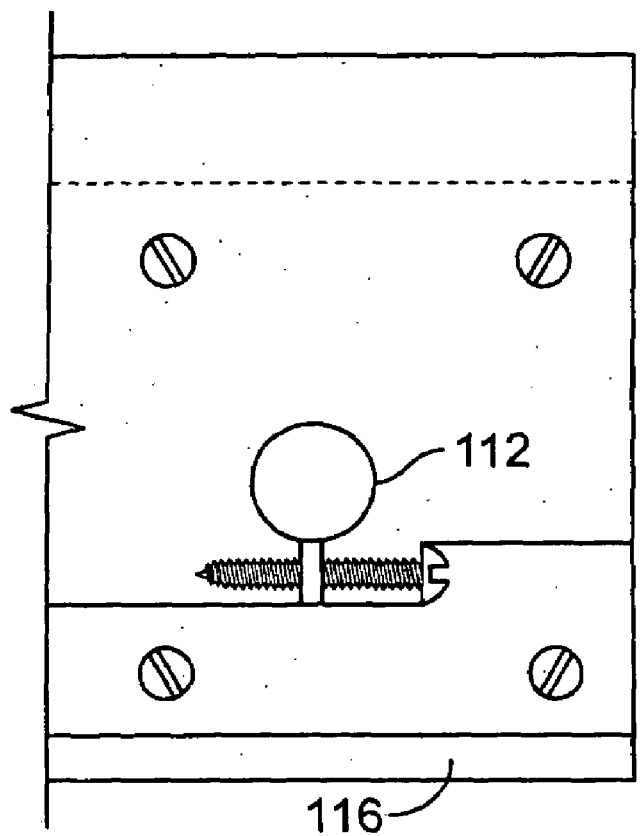

Referring to FIGS. 1C and 1D, in a presently preferred embodiment of a rotary motion reducer, the weak spring force is provided by helical torsion spring 114' of spring constant for instance $K_1$=12 g-cm/radian and the mirror 116 is mounted on a flex bearing 112' such as Bendix #5008-600, having spring constant $K_2$ of 941 g-cm/radian. The torsional spring is selected to have a torsional stiffness $\frac{1}{80}^{th}$ that of the flex bearing, or about 12 g-cm/radian. Thus one step of the stepper motor provides a mirror rotation of about 0.1 milliradian, causing a beam rotation of about 0.2 milliradian.

It is significant that the weak spring-strong spring, rotary stepper motion driven motion divider systems, such as those of FIGS. 1B and C, are immune from backlash, hence are highly accurate, while being simple and inexpensive. The rotary stepper motor readily and accurately reports its position to the computer and the computer accurately directs the stepper motor to the desired angle of illumination or gives instructions that progressively steps the mirror in accurate steps through a range of angles, at each of which the computer calls for the camera to record a wide view image.

Figure 2:
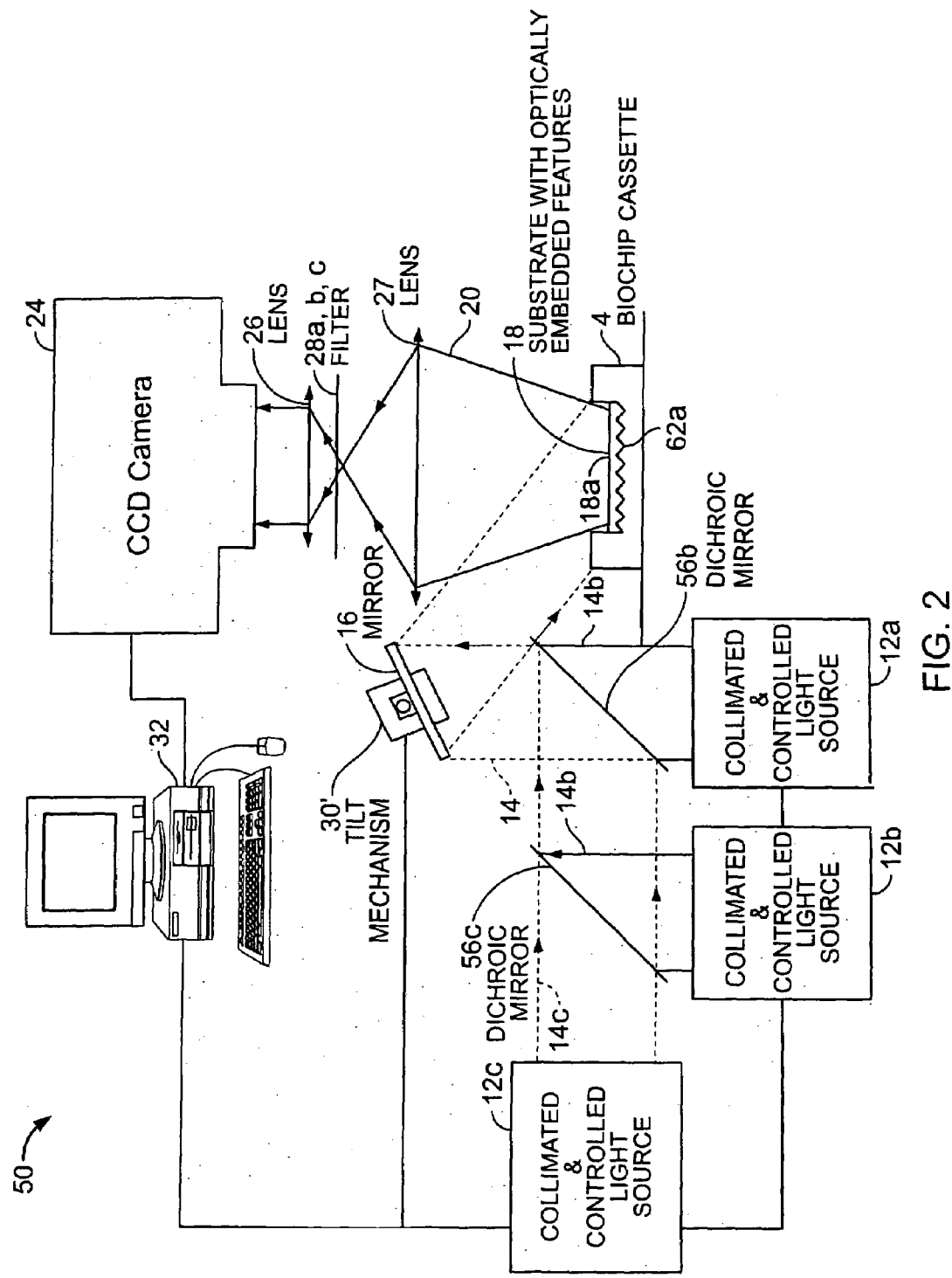
FIG. 2 is a diagrammatic view of an image acquisition microscope similar to that of FIG. 1, but in which the illumination is directed to the top surface of the biochip substrate, and employing internal reflecting features at the bottom of the substrate, opposite the array, to create a surface wave to induce fluorescent emission of an array of tagged biological material samples located on the top surface of the biochip.
Figure 4:
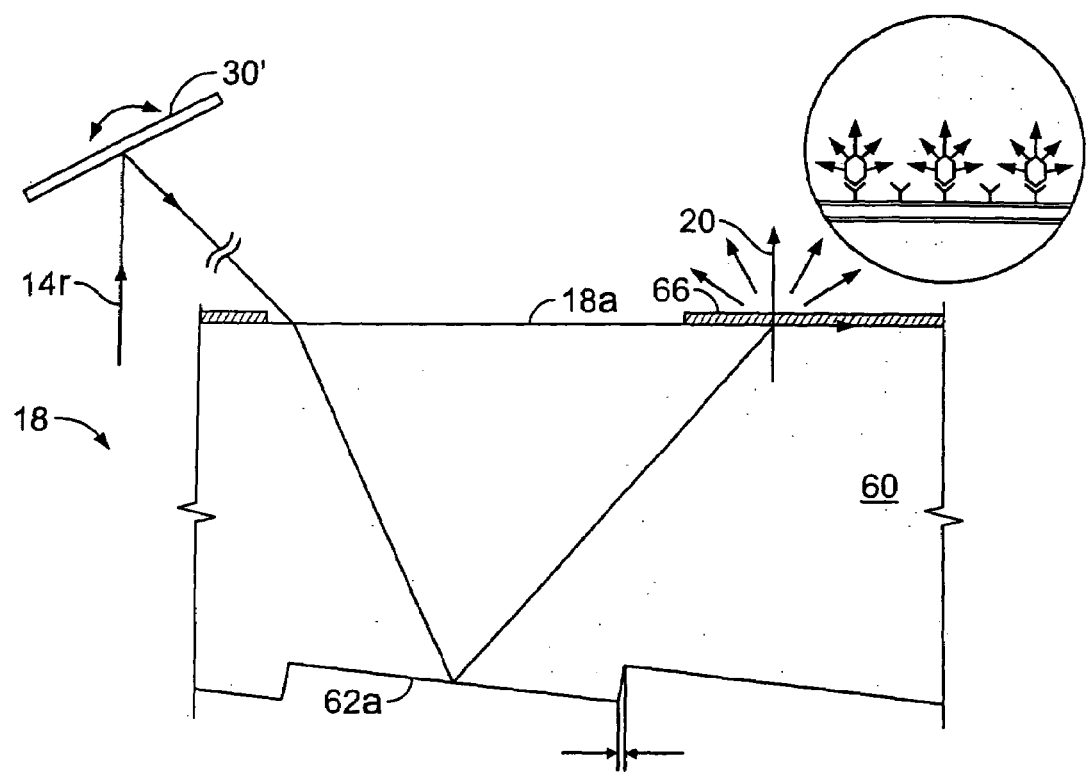
FIG. 4 is a schematic presentation showing the illuminating light path from above striking a support constructed with reflective embedded optical features that stimulate a surface wave and induce fluorescent emission of the tagged area of a biochip.

FIG. 2 illustrates another embodiment of a CCD-based imaging system according to the invention for examination of biological material located on, or near, a substrate having reflective embedded optical features such as shown in FIG. 4. Referring to FIG. 2, optical system 50 includes collimated light sources 12a, 12b, and 12c (and others may be added), each light source equipped with an obscuration device and suitable filters, not shown. These light sources launch beams 14a, 14b and 14c respectively, via associated dichroic beam splitters 56b and 56c, and indexable mirror 16 into the sample substrate 18 via its top surface 18a. The beam 14 is reflected by the reflective features 62a, FIG. 4, at the appropriate angle to induce an evanescent surface wave that stimulates fluorescent emission 20. This emission is captured via lenses 27 and 26 and a filter from the set of filters 28a, 28b or 28c, one associated with each light source and respective fluorescent tag (as before, the filters 28 can be located on either side at lenses 26 and 27). This arrangement permits passage of fluorescently excited light to the camera 24 and rejects reflected ambient light as well as stray light so as to create an image on CCD camera 24. Data from camera 24 is transmitted to computer 32 that analyses the data and actuates mirror tilt mechanism 30' to obtain anticipated signals, initially from selected fiducial reference spots for alignment. The computer program also directs the tilt mechanism 30' to optimize the signal of energy reference spots and defines a best tilt position for illuminating each localized region within the field of view. In some cases mirror tilt mechanism 30' may have two axes of motion instead of the one axis depicted. In preferred cases biochip/support 4 incorporating the embedded optical features has a shape similar to conventional microscope slides, approximately 25 by 75 mm in area and thickness of approximately 1 mm or a few mm.

The light sources 12 that direct light to the substrate having the embedded optical features are selected to emit light of wavelengths capable of exciting selected fluorophores associated with, e.g. tagged to, the biological material to be examined. For example, a light source 12a, 12b or 12c, etc. may be a gas laser, a diode laser or one or a set of LEDs. These may emit simultaneously or sequentially light of 473, 488 and 490 nm wavelength or they may be diodes that emit at 532 nm, 638 nm or 745 nm.

For an example, excitation light of 488 nm excites fluorophores that emit fluorescent light, for example, in the range of 515 nm to 595 nm. Various types of fluorophores (and their corresponding absorption maxima) are Fluorescein (488 nm), Dichloro-fluorescein (525 nm), Hexachlorofluorescein (529 nm), Tetramethylrhodamine (550 nm), Rhodamine X (575 nm), Cy3™ (550 nm), Cy5™ (650 nm), Cy7™ (750 nm), and IRD40 (785 nm). A detector such as CCD camera having 512×512 pixels, associated with suitable band pass or rejection filters detects the fluorescent light emitted from the biological sample on the substrate 18. Preferably, objective lens 26 has a field of view sufficiently large to capture simultaneously an image of all fluorescently active biological material deposited on a wide defined area of surface 18 of biochip 4, e.g. an image area of 15×15 mm. The slide may for instance have two or more regions for wide arrays of deposited biological material. Each image area can be entered sequentially in the viewing area of lens 26, 27 and camera 24. FIG. 3 shows a support according to the invention in the form of a microscope slide with two regions, 18a' and 18a", each with its opposed matching field of embedded optical features.

In another embodiment, not shown, CCD camera is a single line array camera associated with a stage for advancing the cassette in one direction past the camera or vice versa, or it is a multiple line camera, in either case using "time delay integration" techniques, with the cassette or the camera translated in order to capture an entire image of the viewing area of substrate 18.

In FIG. 3, substrate 150 with optically embedded features 62 has approximately the proportions of a conventional microscope slide, i.e. length and width dimensions of 25 and 75 mm, with thickness of approximately 1 mm or a few mm. Sample support surface 18a may be smaller such as a rectangle of 32 mm length and 16 mm width. Surface 18a is shown depressed below peripheral frame 154, the latter providing rigidity to the cassette in an arrangement defining a protective cavity that can be readily closed by a planar film or membrane welded or bonded to the top surface of frame 154. Region 156 at one end, at the level of frame 154, is preferably dedicated to recording information such as serialization for keeping track of the identity of the slide. Surfaces 18a and 154 may be separated by as little as 0.1 mm or as much as 1 mm.

Referring to FIGS. 3A, 3B and 3C, constructed in a transmission geometry the substrate 18 with embedded optical features 62 includes a rigid support body 60 having a top surface 18a on which the biological material to be imaged is located. As shown, the optical features of this embodiment located under surface 18a, comprise, for example, long triangular cross-section grooves having planar sides or facets 63, 63' inclined to be approximately, sequentially, normal and parallel to the critical angle α associated with the surface wave of interest at the mid range of critical angles associated with it. Surfaces 63 receive illumination rays 14r of the broad collimated or quasi-collimated illumination beam 14. The critical angle for surface 18 a is defined by the selected wavelength of excitation light λ, the index of refraction $n_s$ of the selected substrate material 60 and the index of refraction $n_m$ of the chosen biological material 66 and the index $n_c$ of any coatings on the deposit surface such as coatings 70 or 72, FIG. 3C. Coating 70 in FIG. 3C is a symbolic representation of a coated structure that may include a succession of higher and lower indices of refraction coatings selected to establish a wave guide according to known techniques, in which a surface wave 74 may be captured. Final coating 72 may be chosen to best bind and optically couple to the desired biological material as well as to the below structure, and may, for instance, be a thin layer of polystyrene. The mirror 16r in FIGS. 3–3G is a "representation" mirror for explanation purposes. The actual mirror 16 is much larger, relatively as shown in FIG. 1, being sized to reflect the entire broad illumination beam 14 to cover the entire field of embedded optical features, corresponding in size to the area 18a' or 18a" to be imaged, e.g. 15×15 millimeters of the presently preferred example.

FIG. 3D illustrates a film 160 in which embedded optical features 62 are formed by casting or embossing the film 160, which is then adhered to support member 162 such as a microscope slide or plastic member, via transparent bonding agent 164. Agent 164 fills the grooves, only one shown, and binds the film to the support. Other means of attachment may also be employed, for instance bonding regions located outside the region reserved for deposit of the biological matter with the ridge formations of the film supported in planar array by contact with a surface of support 162. The thickness of support 162 may be significantly than the film thickness to perform a stabilizing, supporting function.

Figure 3E:
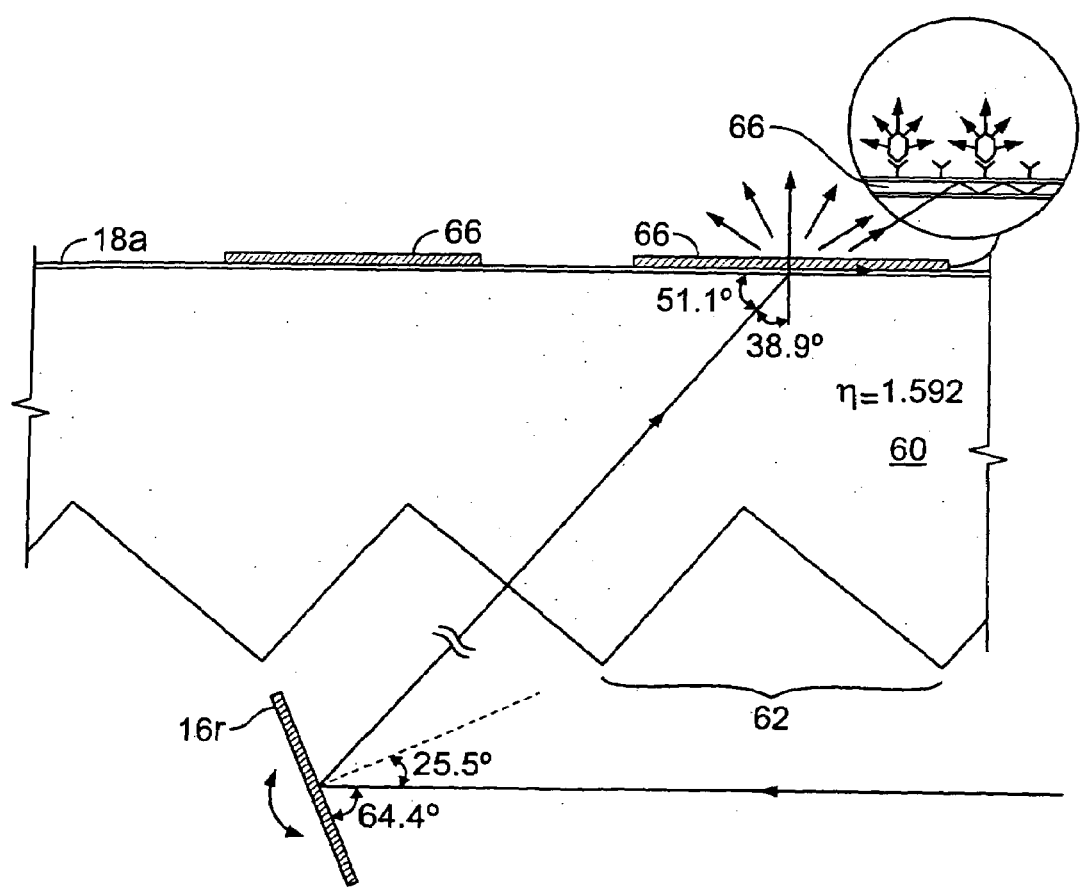
FIG. 3E is a schematic presentation similar to FIG. 3B, in which the sample itself forms a Fabry Perot cavity for the light at the exciting wave length.
Figure 3F:
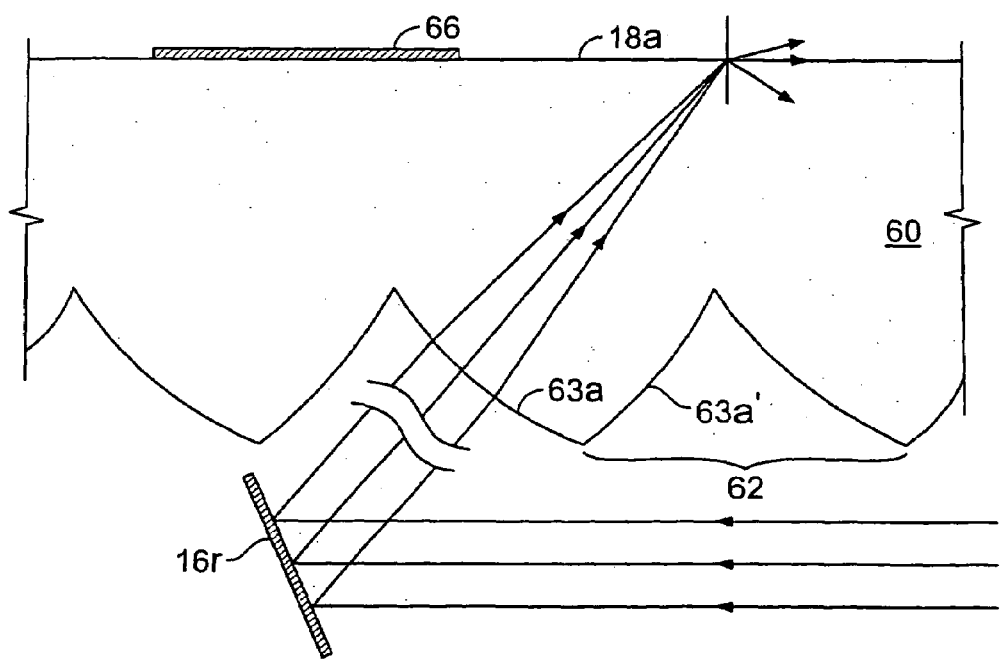
FIG. 3F is a schematic, exaggerated illustration of an alternate construction in which the embedded optical features have surfaces that are not flat.
Figure 3G:
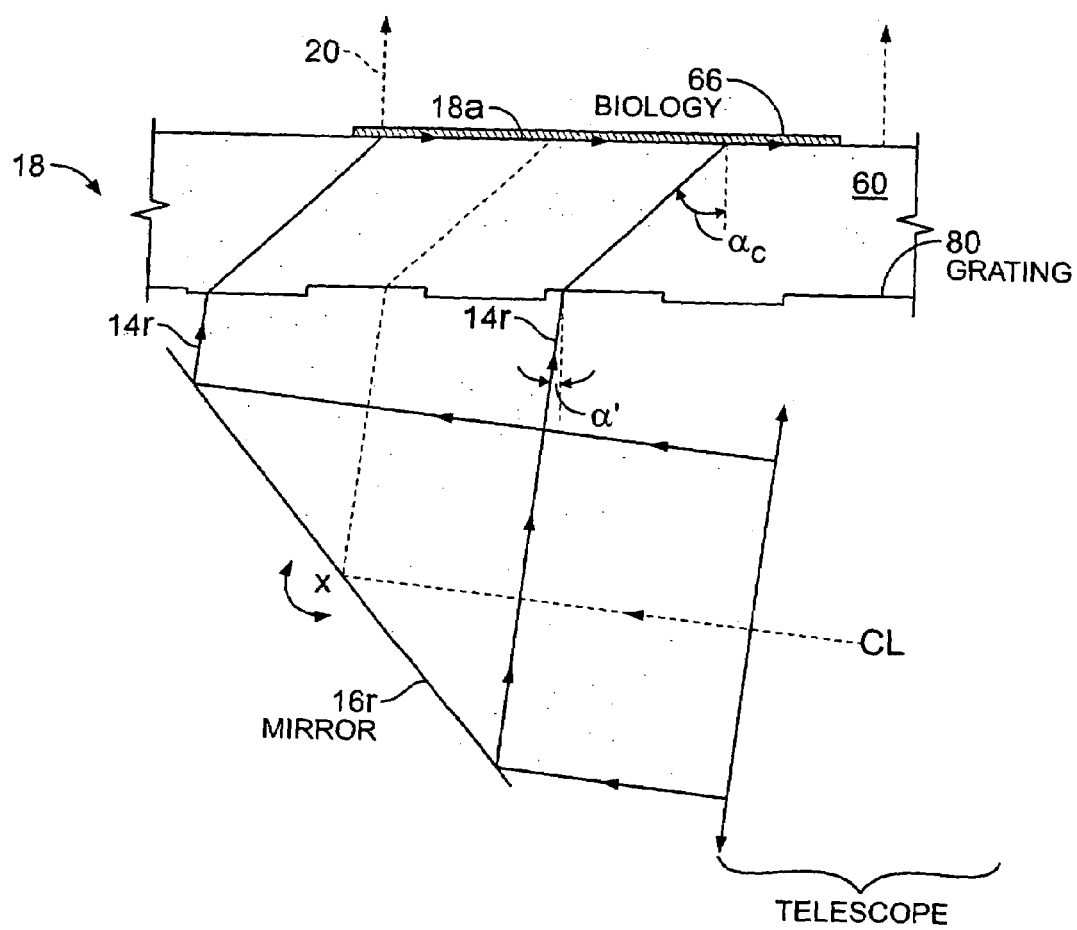
FIG. 3G is a schematic illustration of an alternate construction in which the embedded optical features opposite the array are in the form of a diffraction grating that is illuminated at an acute angle.

FIG. 3E illustrates the case in which the thickness of the deposited biological material 66 itself is selected to act as the spacer of a Fabry Perot resonant cavity for the illumination wave length, such that the light propagates laterally in resonant manner inside the thickness of the sample spot as it is absorbed. A coating matching the index of refraction of the sample is included to cooperate with the sample thickness to achieve the appropriate spacer dimension.

As shown symbolically in FIG. 3E (curvature greatly exaggerated) surfaces 63a, 63a' may deviate from perfect flatness in order to induce a multiplicity of incident angles to rays of beams 14 at surface 64 to accommodate local variations of critical angle due to material or geometric variations. These surfaces, i.e. the facets receiving the illuminating rays, may be shaped as shallow cylinders, ellipsoids, paraboloids or hyperboloids to produce an angular variation of the refracted light rays within approximately 1 or 2 degrees.

According to one embodiment, the optical plate 60 of FIG. 3A is made of an optically transparent material such as polystyrene, polymethylmethacrylate (PMMA) i.e. Plexiglas™ or a similar plastic. Embedded optical features 62 may be created in plate 60 by forced embossing a selected thermoplastic of a temperature above its characteristic softening temperature, or by casting the plate against a suitably formed negative master or a combination of both according to known techniques employed in manufacturing CD and DVD discs from masters. Alternatively, plate 60 and the embedded optical features or microelements 62 are formed of etched glass, etched quartz or other suitable optical material. The embedded optical features may also be created by compression or embossing especially a very thin support, preferably using heat to soften the material, the embossed film then being mounted in planar orientation across a rigid frame.

The support body 60 may have thickness approximating that of a microscope slide, 1 mm or a few mm, or may be thinner and may have ridges, e.g. in the region between viewing fields to increase its rigidity. Support body 60 may be very thin, as thin as 25 micro-meter with micro groves 62 in this case with period less than e.g. 1 micron. The thin support 60 may be supported on a more rigid base to which it may be attached with a bonding agent or may be welded or fused to it about its perimeter.

Regardless of the type of construction, as previously mentioned, support 60 is preferably shaped to the familiar form of a microscope slide, 1×3 inches (25×75 mm) to be capable of handling in manner similar to the handling of microscope slides.

For an alternate construction for use in the reflective system of FIG. 2, features 62 are formed e.g. by casting into the upper surface of a structural base such as support 162 of FIG. 3D. Features 62 are then coated with reflective film by vapor deposition, and then, to form the support 60 for the biological sample, the reflective features are over-coated with a material of similar index of refraction, such as silicon monoxide or silicon dioxide or by spraying a dissolved thin coating of transparent plastic such as PMMA, in manner to result in a planar upper surface suitable to receive the biology.

Another important aspect of the invention is the provision of strategically located intensity reference spots to be used for energy calibration, for comparison with deposited biological material, and where desired, for use in selecting the optimum illumination angle for the image of each local region of the field of view of the images based on the actual response of an energy reference spot in each respective region. By judging the responses for each local region in a series, a "quilt" composite image of best responses can be prepared from selected local regions of the various images. These energy references may be of biological nature or other organic or of inorganic matter, preferably sufficiently thin to be transparent. A preferred choice may be made from a variety of polyamides such as Kapton. Numerous materials are marketed under the trade name of Kapton™ and have different fluorescent emission. The preferred choice is the form of Kapton™ available in liquid form and used for spin coating, such as can be obtained from Arch Chemical or DH MicroSystems. It has good adhesion properties. The reference material in solution in a volatile solvent (as well as the biological samples themselves) can be spotted (e.g. pin deposited) from wells of a conventional well plate using spotting techniques, for instance the techniques as disclosed in U.S. Pat. No. 6,269,846 (Overbeck et al.), the entire contents of which are hereby incorporated by reference. Also since the fluorescent properties of polyamides vary substantially in predictable manner according to grade of the material, samples of the material of various selected properties can be deposited on a support and used to calibrate the dynamic range of the imaging system at various spectral bands. An alternate energy reference material is a thin layer of fluorescent glass, deposited e.g. by evaporation, according to known techniques, or a fluorescently labeled biological material of controlled luminescence.

Referring to FIG. 3G, the embedded optical features are shown in the form of a diffraction grating 80 illuminated at an acute angle $\alpha'$ to the normal, e.g., an angle of 10 or 15°. The collimated beam 14 is reflected from mirror 16r, such that the rays 14r proceed from the grating at the critical angle $\alpha_c$ to form an evanescence wave at the biological sample. As before, rays 14r reaching top surface 18a are slightly offset from the point of entry into support 18. This offset, of the point where the ray contributes to a wave propagating along the surface, is slight, defined by the inclination of the critical angle to the surface and the thickness of the substrate which the ray traverses. In this case of a grating and more generally with any of the fields of embedded optical features that are described herein, in preferred embodiments, the evanescent wave or other surface wave effect is essentially created in the area of the biological array itself, by the field of embedded optical features lying under, preferably entirely directly under, the array, not at a separately defined region.

By addressing the grating of FIG. 3G at a non-normal angle, rays 14 of illumination beam 14, that may penetrate the support 16 along their original direction, pass out of the path 20 of fluorescent emission collected by camera 24, and hence do not add perturbations to the results.

With this arrangement, as before, the tilt mechanism 30 may be stepped to obtain wide images at each of an incremented set of angles if desired to form a "quilted" or composite image e.g., by the technique as described further below. This is the case also with the reflective geometry illustrated in detail in FIG. 4, in which refraction of the entering beam by the body 60 of support 18 as well as the angle of reflection at the fine embedded optical feature 62a determines the arrival point of the beam at the surface 18a where the deposited array resides.

Figure 5:
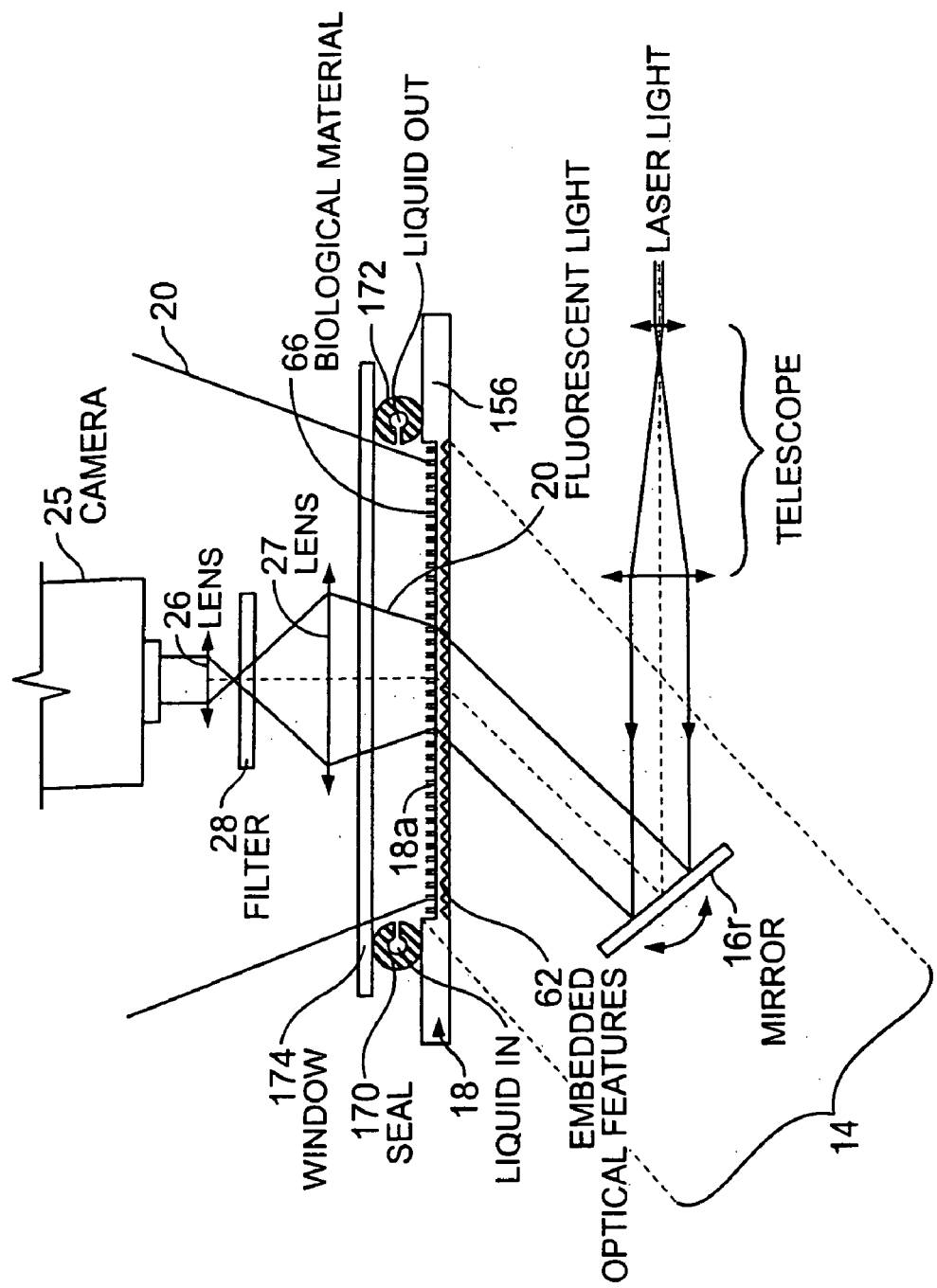
FIG. 5 is a diagrammatic cross-section of a flow cell or cassette that includes a support with a field of embedded optical features positioned for reading in the system of FIG. 1. (The cassette is shown magnified in size relative to the other components for ease of visualization.)
Figure 6:
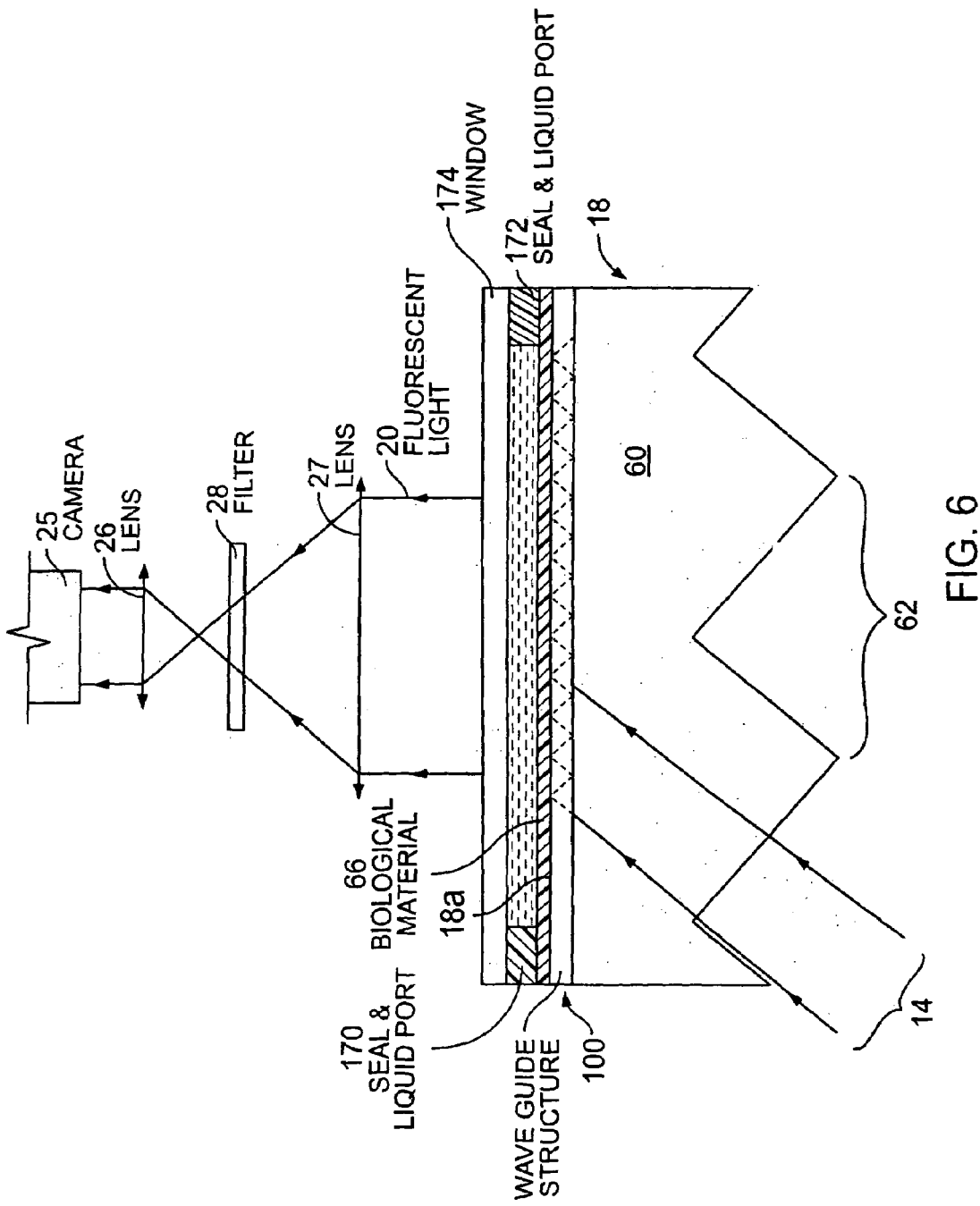
FIG. 6 is a view similar to parts of FIG. 5, showing a different type of cassette, shown even more magnified in size relative to the other components of the system.
Figure 6A:
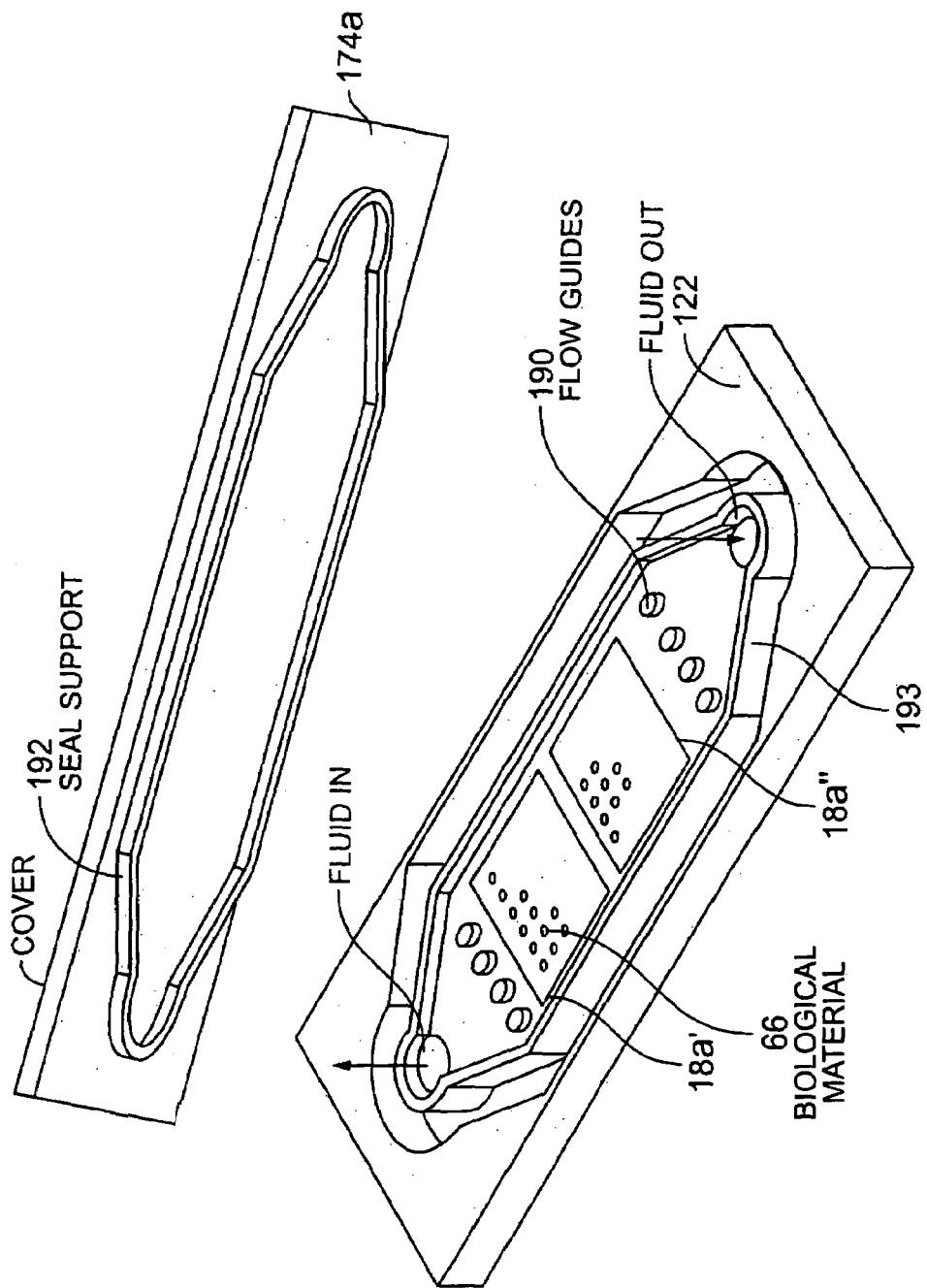
FIG. 6A is a perspective view of exploded parts of another cassette which can be read with the system of FIG. 1.

The embodiments of FIGS. 5, 6 and 6A illustrate flow cells formed with a support according to the invention.

In FIG. 5, a support 18 defines an upper sample array receiving surface 18a and directly under it is a correspondingly sized field of embedded optical features 62 of the transmission type, as previously described. A frame or rim 156 surrounds the area and is constructed to provide a seating surface for linear seals 170, 172, which form a perimeter seal with support 18. The seals also seal to the overlying transparent window 174. These elements together define a reaction chamber 176, into which reagent and washing fluids can be introduced via hollow passages in seal 170 and removed via hollow passages in seal 172.

This cell is placed in the imaging system of FIG. 1, and is illuminated from below by mirror 16, represented in the figure by a smaller mirror icon, 16r in the figure. By this means collimated or quasi-collimated illumination beam 14 is addressed to the field of embedded optical features at a selected angle determined by computer 32 and the tilt mechanism 30. The imaging may be performed when the chamber 176 is empty and the biological material 66 dry, or when wet, either while flow through the cell occurs or when the fluid is quiescent. In any of these cases, the excited fluorescence light 20 is collected after passing through the transparent window 174, and proceeds to the camera as before. The discussion above related to the operation of the system of FIG. 1 and the description of the support 18 of FIGS. 3A and 3B relate to the operation of the embodiment of FIG. 5 as well.

Though different in specific construction features, the flow cell of FIG. 6 is essentially the same as that of FIG. 5, except in this case, as was the case with respect to the embodiment of FIG. 3C, coating 70 adjacent the upper sample surface 18a defines a wave guide along that surface, along which the light propagates by successive internal reflections, while its evanescent field excites the fluorophores of the material at surface 18a. As with FIG. 5, FIG. 6 is diagrammatic and it is to be understood that the entire field of the embedded optical elements is illuminated by beam 14 and camera 25 collects the luminescent rays 20 from across the entire width of the sample field.

The embodiment of FIG. 6A is different from the foregoing cells in known ways, i.e. the transparent window 174a carries a sealing element 192 that seats in a matching channel defined in the base 122, and flow guides 190 are included to distribute and make uniform the fluid flow across the two arrays provided on surfaces 18a' and 18a". Fields of embedded optical elements 62 of dimensions corresponding to the image areas 18a' and 18a", lie directly below those areas. As with the other flow cell embodiments, the optical features may have any of the forms described above with respect to transmission illumination of the sample, and the system may perform based on producing an evanescent surface wave launched at the critical angle, or a wave guide effect along the surface 18a, or the Fabry Perot cavity effect of the sample, or combinations of these as well as other effects at the surface.

In the case of the flow cells of FIGS. 5, 6 and 6a, as well as the embodiments of the FIGS. 3–3e, a point has been made of the preferred directly opposite relationship of the field of the embedded refractive and reflective optical features 62 and the deposit areas 18a for the biological arrays. Indeed, such relationship is important in achieving compact cassettes and flow cells, in form with which the scientific workers and laboratory technicians are familiar and which can be handled by existing robotic equipment. Nevertheless, it must be understood that numerous important features of the invention can be employed to advantage with other constructions of the substrate, in which, for instance the fields of the embedded optical features under the array-supporting surface only partly overlap with the mating sample arrays, or indeed, where compactness is not a requirement, separately defined regions for the tiny transmissive or reflective embedded optical features and the deposit areas may be employed. Even in the case of matching the general form of a microscope slide, it is feasible to utilize substantially the entire facial area of the slide, i.e., use also the region commonly devoted to serialization as additional area on which to locate the embedded optical features, the array deposit surfaces or both. While it is presently preferred to employ bottom illumination, and reading from the top, out of mechanical spatial considerations as well as to avoid subjecting the light to a double pass through the material 60 of the support, it will be understood that top lighted versions of the cells of FIGS. 5, 6 and 6a, modified according to FIG. 4 and viewed according to FIG. 2 are feasible and in some instances may be preferred out of other considerations.

A great deal has been mentioned herein about the ability to take images through a series of incremented illumination angles, and indeed that is a vital aspect of robust implementations of the invention that have the capability to handle a wide range of biological and even inorganic samples, using a wide variety of fluorescent tags and the like. We will include more details of the preferred implementation of this feature, and its considerable advantages. But here again, the reader should understand that the invention in many of its broader aspects is not limited to that important feature. Single angles of illumination and single images potentially have their place in certain circumstances, for instance in cases where all materials, shapes and dimensions are suitably defined at the appropriate level of precision, or in cases in which a single use instrument is all that is needed, as for instance in quality control uses in manufacturing, meat packing, water quality and the like where only "yes" or "no" information may be required.

Referring now to FIGS. 7, 7a, 7b, 8 and 9, a preferred implementation of the image acquisition aspects of the instrument of FIGS. 1 and 2 at various illumination angles over an incremented range will now be described.

Figure 8:
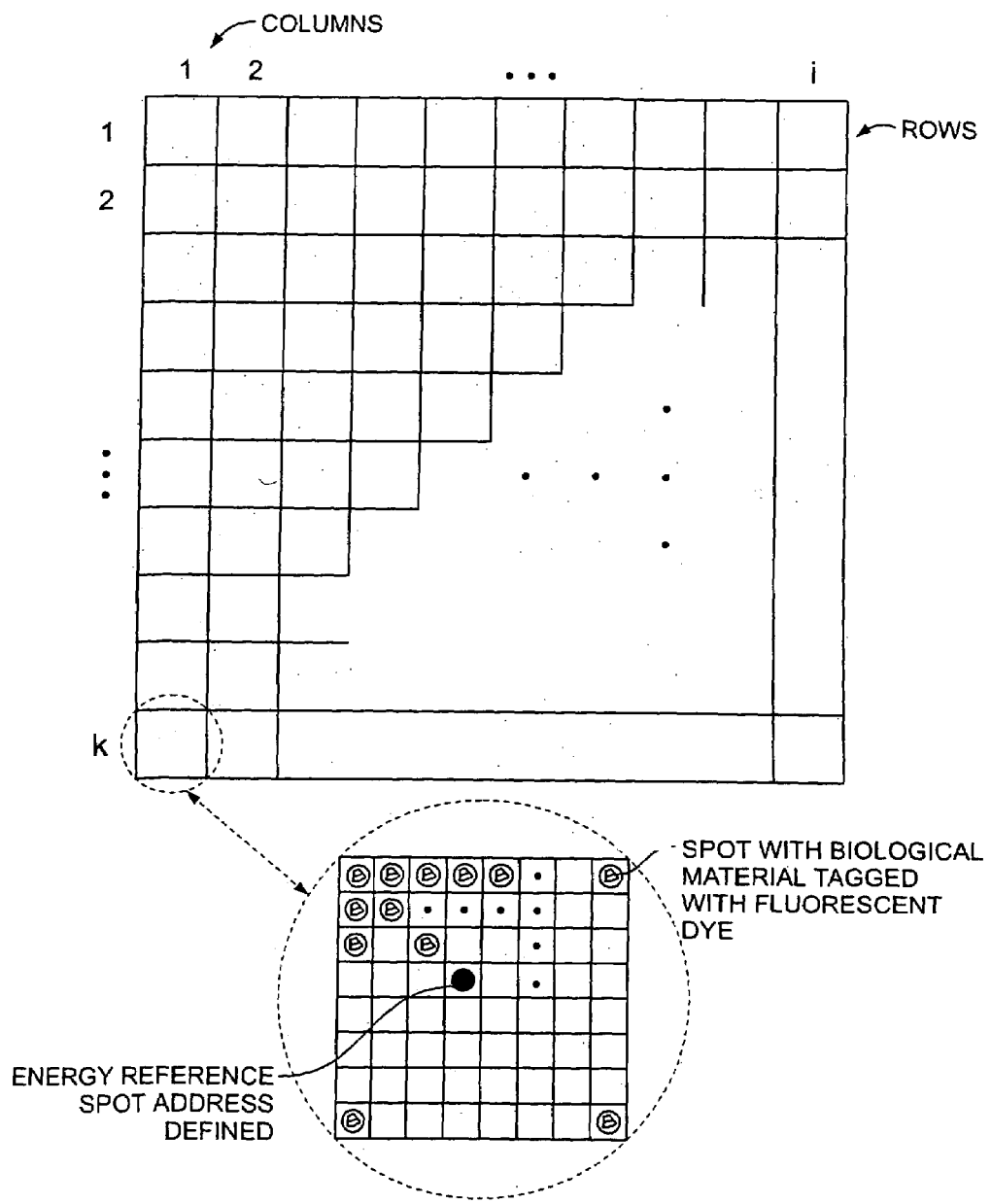
FIG. 8 illustrates the final wide field of view quilted image and its component regions derived from selected sub-regions of a series of full field of view images.
Figure 9:
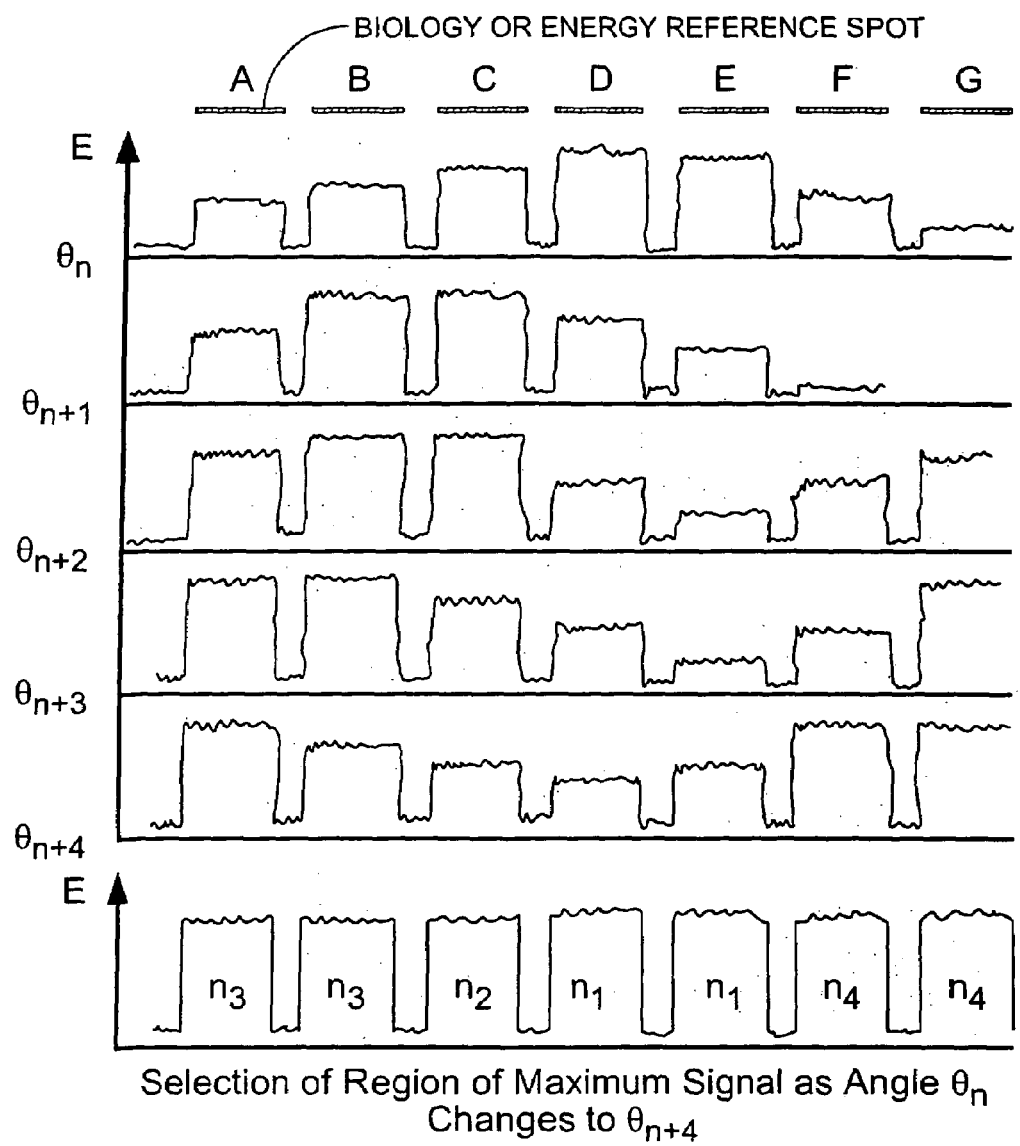
FIG. 9 is an illustrative diagram of signal responses obtained in wide field images taken at a series of illumination angles.

As previously indicated, referring to FIG. 8, a single wide area image taken at a single illumination angle θ by the camera 25 may be conceptually broken into a matrix of localized regions, e.g. regions extending in rows 1 to k and in columns 1 to i, as suggested by the figure. According to a feature of the inventions, each localized region is associated with one or more energy references, e.g. spot E in the middle of the region k,1, and like spots in each of the other regions, or a bracket of two such spots, or such spots both in the center and at all four corners of each localized region, with the regions overlapping by one spot in all directions, or such spots in other advantageous patterns. By standardizing the fluorescent characteristics of the energy reference spots, i.e., ensuring they are of the same area or volume and contain the same number of fluorophores responsive to the selected wavelength, one can judge the effectiveness of a given angle of illumination over the entire field of embedded optical features and the biological array, by observing the measured response of the various energy reference spots across the array. It will be understood if there is a slight bow in the support 18, or other slight physical difference in planarity or angle of the plane in various regions over the array, by stepping the illumination mirror 16 through a series of adjacent illumination angle increments by tilt control mechanism 30, and observing the response of the energy reference spots over the array of localized regions at each angle, variation in that energy response is likely to be obtained at each of the references over the field of localized regions. For instance the measured responses of the reference spots might vary as depicted in FIG. 9, in which maximum signal for one particular angle of illumination for one localized region, may correspond to a relatively poor response at that angle for other localized regions, and vice versa.

Rather than be discouraged by such variation, especially in the case of low cost substrates, according to the invention, advantage is taken of the good responses in parts of one image; other images are taken at adjacent angles and are inspected for other localized regions of good response, and a best set of such responses is determined from the set of images over a set of adjacent illumination angles to provide a composite or "quilted" final image that maps the energy reference spots, and with high likelihood, will be indicative of the proper angle of illumination for obtaining maximum response for the neighboring sample spots.

Figure 7:
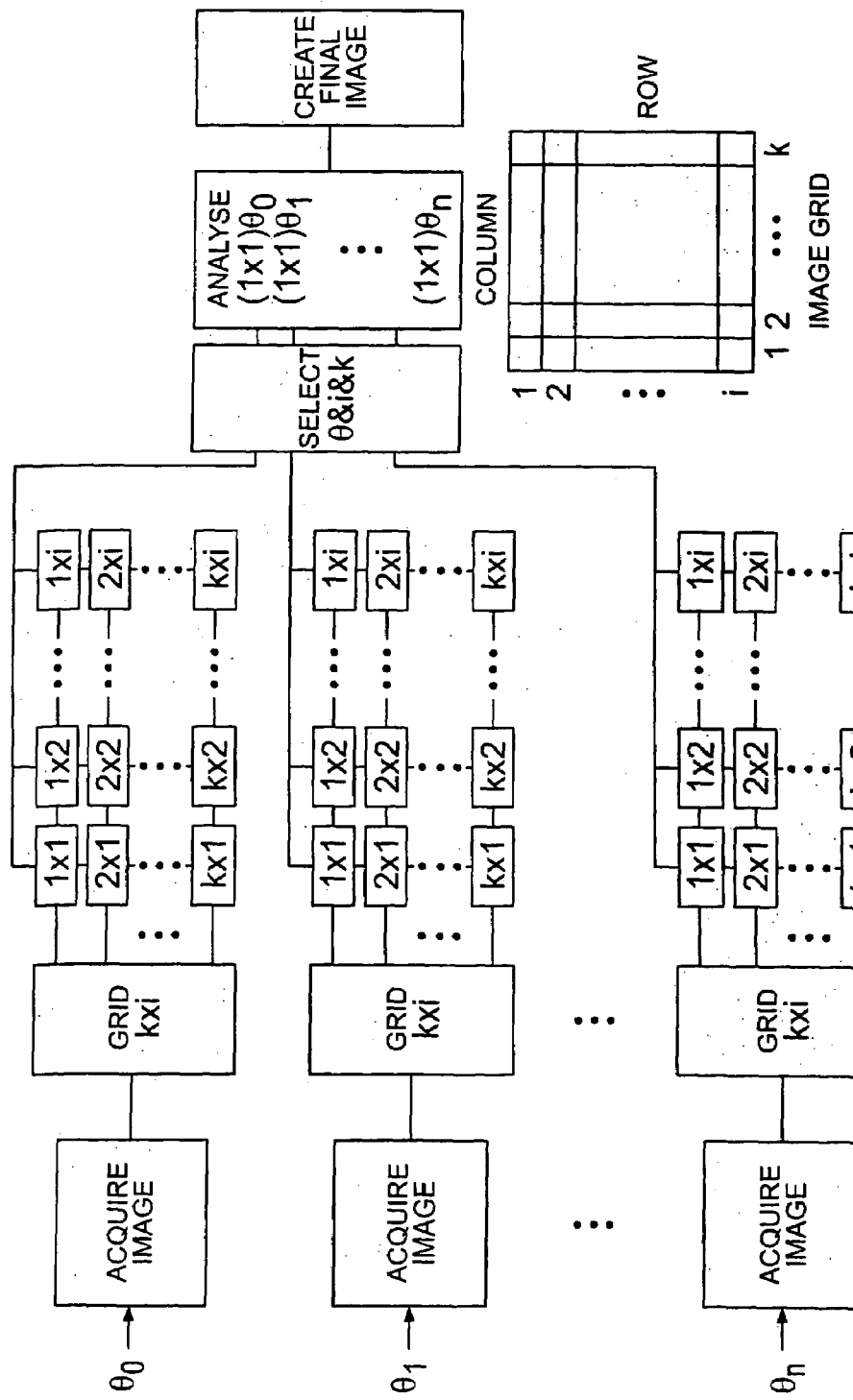
FIG. 7 is a diagram illustrating image acquisition and analysis steps performed by the system of FIG. 1.
Figure 7A:
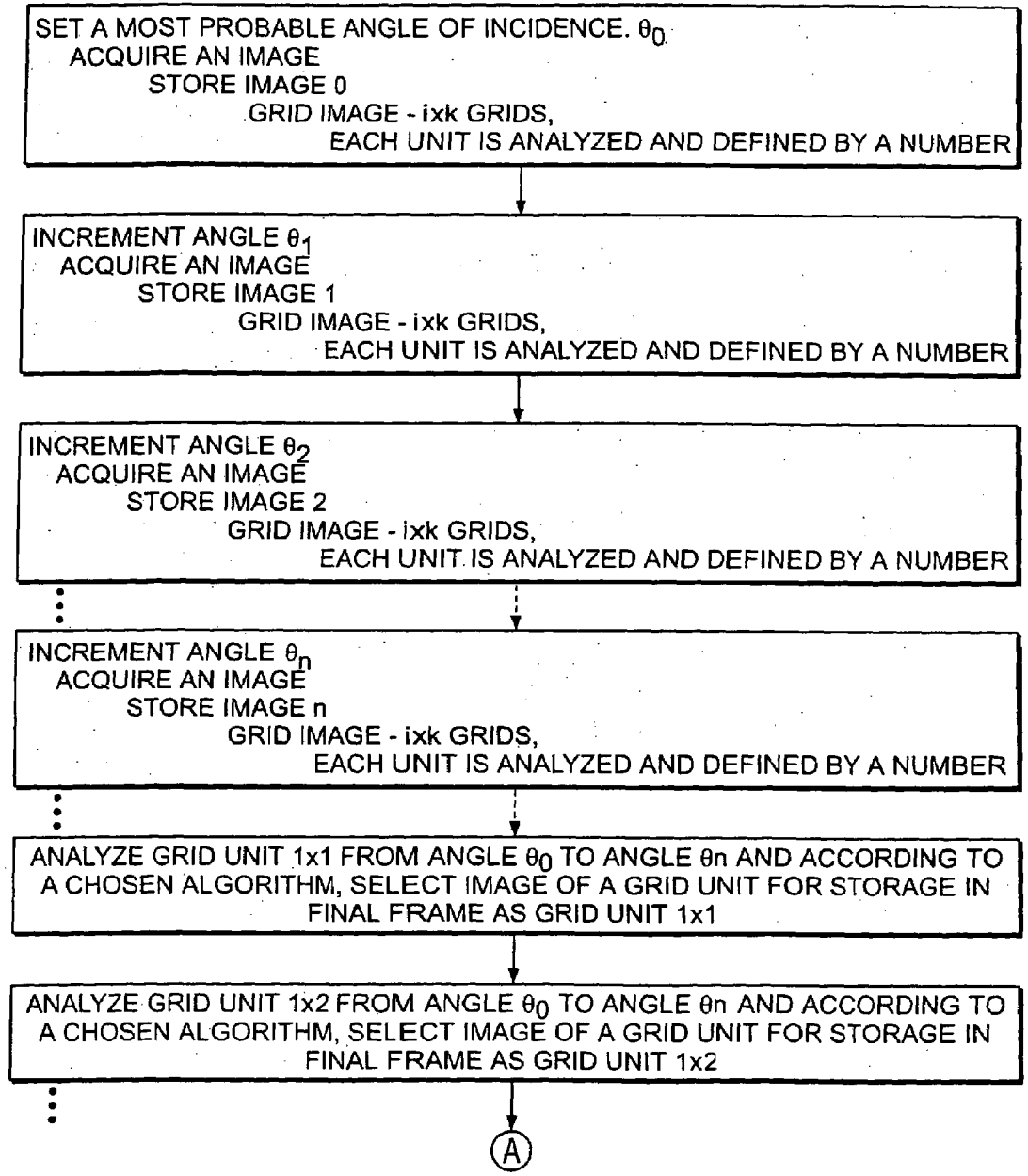
FIGS. 7A and 7B are successive parts of a flow diagram at a more detailed level of the steps illustrated in FIG. 7.
Figure 7B:
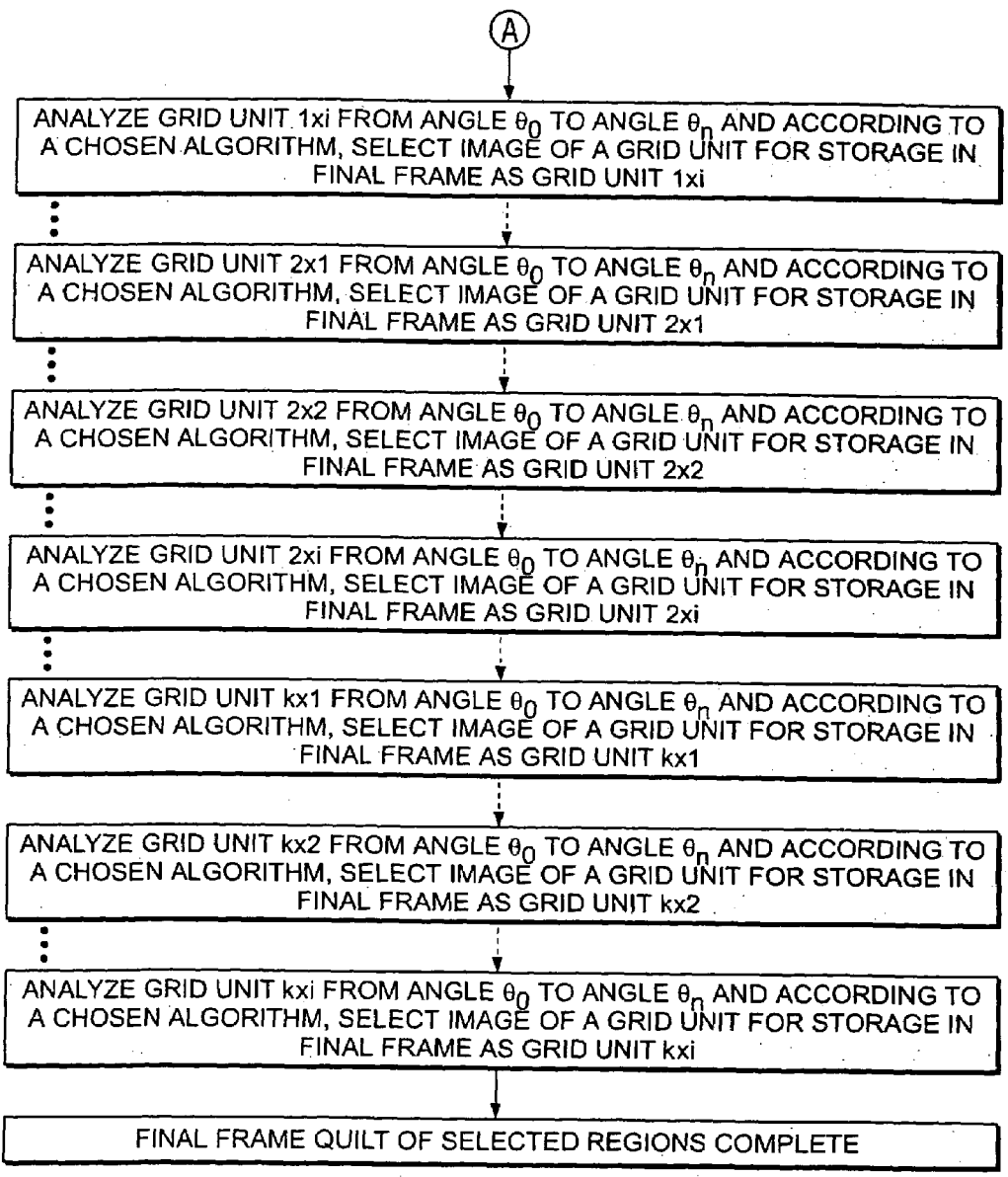

Referring to FIGS. 7, 7a and its continuation FIG. 7b, by an initial protocol, or from past experience, a most probable angle of incidence of the illumination beam is determined for achieving best response for the entire array, and the substrate is inspected at angles including that angle, and at closely adjacent angular increments on one or preferably on both sides of that probable angle. For simplicity of the example, increments on only one side of the optimum are used in the flow diagram of FIGS. 7a and 7b. The flow diagram is then self explanatory, in that a full image is taken at each incremented angular position of the illumination mirror 16, and the matrix of responses from the reference spots for localized regions that represent that image is evaluated according to a selected algorithm. At an illumination angle a in which the reference values respecting some of the localized regions are highest, in comparison to the responses for those regions illuminated at other angles, forming other images of the set, the actual measured values of the spots in the respective localized regions illuminated at angle a are taken as best, and assigned to the final quilted matrix of responses. This evaluation is made with respect to each of the localized regions, comparing in each instance the responses from the energy references for the respective localized region over the set of images, and picking the data from the localized region whose energy reference spot(s) have highest value.

In the manipulation of the data to produce an equalized version of it, instead of taking the raw data, the data for each spot over a localized region may be evaluated using the value of the respective local energy reference spot(s) as unity, and using percentages of such a comparison as the detected values of the various spots in that region.

Depending upon the needs for precision, and the number and character of the set of energy reference spots employed, more sophisticated evaluation systems may likewise make use of the various concepts of employing localized regions of an image associated with fluorescence energy references according to well understood sampling and comparison theory.

Figure 10:
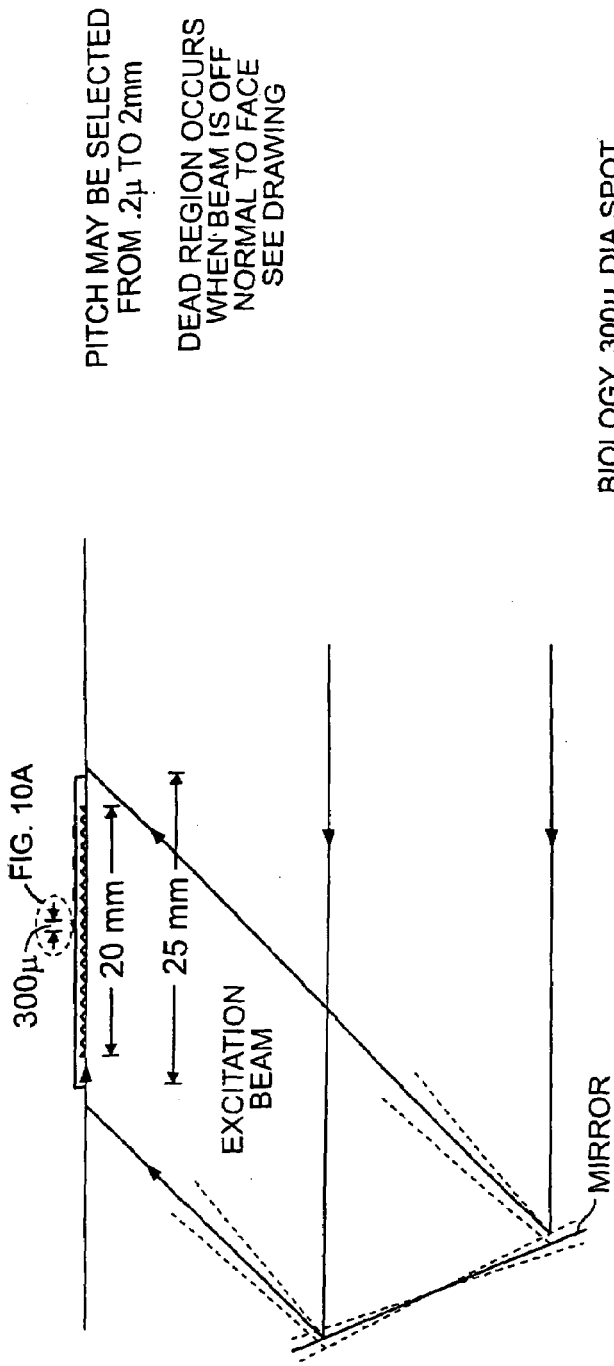
FIGS. 10, 10A and 10B illustrate at successively larger magnifications the obscuration effect obtained at edges of embedded optical features and the relationship of such artifacts relative to a sample spot.
Figure 10A:
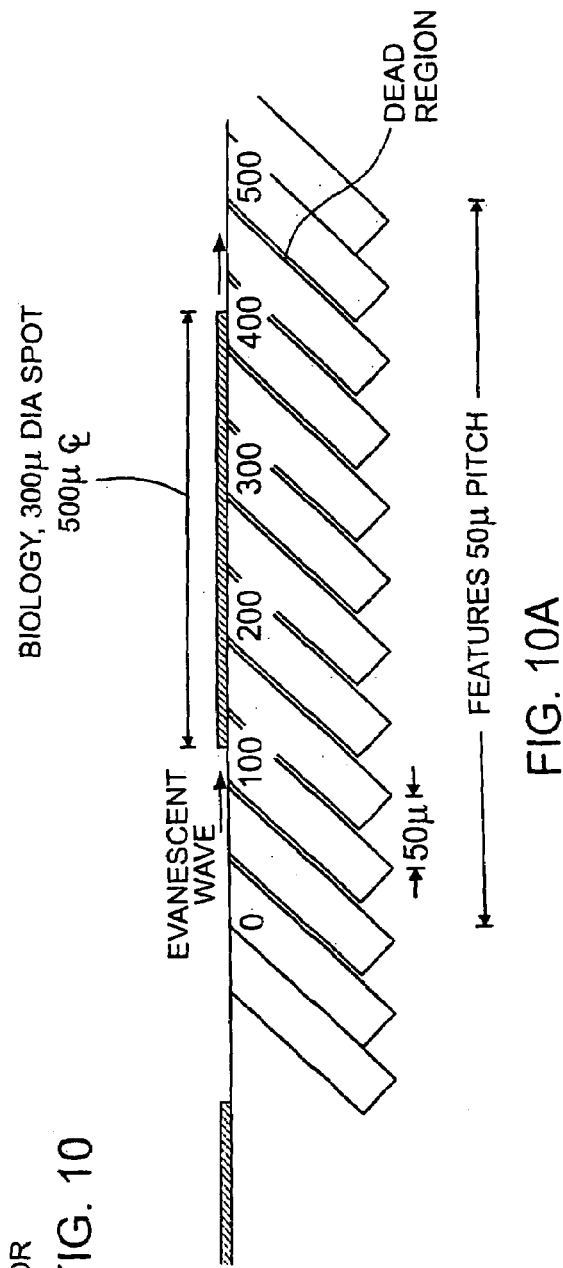
Figure 10B:
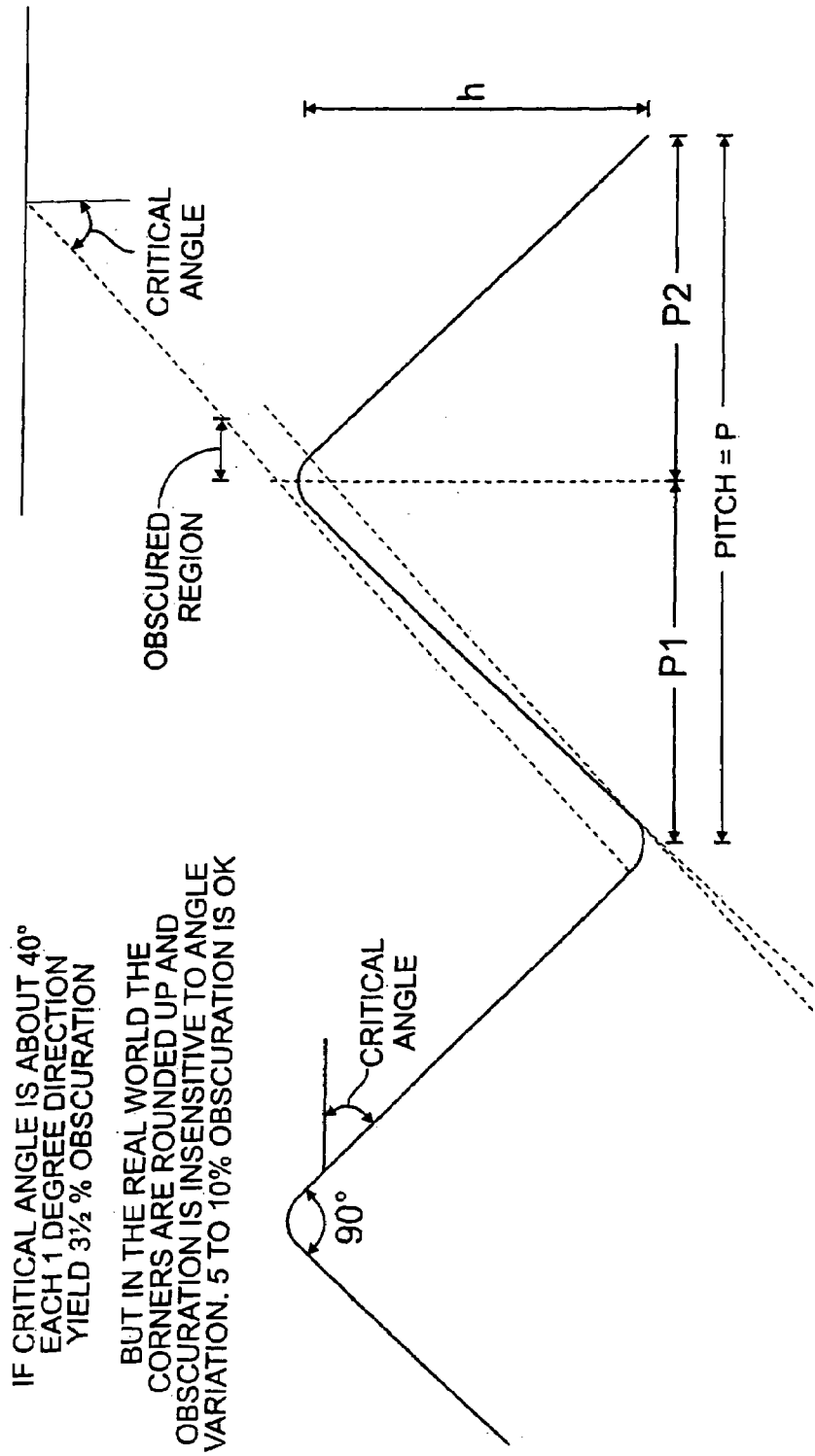

Referring now to FIGS. 10, 10A and 10B, the obscured region associated with the edge of an embedded optical feature in the case in which the illumination rays are not precisely perpendicular to the facet of the feature is graphically illustrated. It is seen that the "shadow" that such an edge casts has a width that increases the longer the distance from the optical feature to surface 18a. Likewise, it is seen that the more numerous such shadows that fall upon sample spots of a given size, the less the variation will be if one spot receives one more shadow than another. According to the invention, it is realized that there is an effective region, in which the embedded optical features are not too large to cause serious artifacts in comparing one sample spot to another, and not too small, to what would detrimentally increase the amount of area occupied by edge regions; in general, with the optical features in the range of about $1/4^{th}$ to $1/50^{th}$ of the size of the spots, the obscuration effect is realized to be consistent with still obtaining results with good accuracy, the preferred value being of the order of $1/10^{th}$ the size of the spots for the smallest spots.

From the above general discussion and the detailed description of presently preferred embodiments and the following claims, the new techniques of the invention will be understood. Accordingly, numerous other specific embodiments will occur to those having skill in the art within the spirit and scope of the claims.

What is claimed is:

1. A support for an array of fluorescently labeled samples comprising a transparent body that enables imaging of the array, the transparent body defining:
   (a) sample-receiving array-support surface disposed to receive an array of the labeled samples, the surface adapted to enable a surface wave effect to travel laterally in the transparent body adjacent the surface and
   (b) a field of embedded optical features located below and spaced from the array-support surface so that light reaching the optical features must then pass through the transparent body to reach the support surface and the labeled samples,
   the field of optical features, exposed to be illuminated by a broad light beam of excitation radiation,
   the field of optical features and the support being constructed and arranged so that a light beam addressed to the optical features can be launched through the transparent body at an acute angle to said sample-receiving array-support surface to produce a surface wave effect that travels laterally in the transparent body adjacent the surface,
   thereby to excite fluorescence from the array of samples to enable an image of the fluorescing array along an axis independent of the angle of the beam of illumination.

2. The support of claim 1 in which said support surface is an uninterrupted planar surface that bears spots of sample of spot size between about 50 and 500 micron.

3. The support of claim 1 in the form of a microscope slide constructed to enable imaging of the support surface alone an axis normal to the support surface.

4. The support of any of the claims 1 in which said support surface defines a wetted surface of a flow cell, the flow cell having a window for viewing fluorescence from said support surface, and the field of embedded optical features is unwetted.

5. The support of any of the claim 1 in which said embedded optical features are exposed for illumination by a beam directed toward the side of the support opposite from the array-support surface.

6. The support of claim 5 in which said embedded optical features comprise transmissive facets disposed at an angle to the array-support surface and substantially at right angles to the general direction of the selected beam.

7. The support of claim 6 in which said angle of said beam lies between about 30 and 60 degrees to the normal to said array-support surface.

8. The support of claim 7 in which said angle of said beam lies between about 38 to 44 degrees to said normal.

9. The support of the claim 6 in which said optical features are defined by sides of triangular grooves.

10. The support of claim 5 associated with an imager having an axis normal to the support surface and in which said optical features define a diffraction grating arranged to receive an illuminating beam at an angle substantially less than perpendicular to said support surface.

11. The support of claim 1 in which said embedded optical features comprise reflective surfaces exposed for illumination by a beam directed toward said support surface.

12. The support of claim 11 in which said reflective surfaces are defined by sides of triangular grooves.

13. The support of claim 1 in which said optical features are so defined and arranged in a pattern to accomodate variations in the critical angle of said array-support surface.

14. The support of claim 1 wherein the body of said support is substantially comprised of disposable plastic.

15. The support of claim 14 in which said disposable plastic is polystyrene, PMMA or polycarbonate.

16. The support of claim 1 wherein said embedded optical features comprise features of an article cast of molten material in a mold.

17. The support of claim 1 wherein said embedded optical features comprise features that are embossed or press-molded.

18. The support of claim 1 having a plurality of coatings or layers along said array-support surface, the array-support surface comprising a layer of a substance capable of adhering to an adjacent lower substance of the support and to the samples.

19. The support of claim 18 in which said outer layer comprises polystyrene.

20. The support of claim 1 having a plurality of coatings or layers along said support surface that define a wave guide for a wave propogating along that surface.

21. The support of claim 2 having reflective or transmissive embedded optical features, said support surface being adapted to receive samples of a predetermined minimum spot size, the size and periodicity of said features being in the range of about ¼ th to ⅕₀th said spot size.

22. The support of claim 21 wherein said size and periodicity is of the order of ⅟₁₀th said spot size.

23. The support of claim 1 in which the portion of the array support surface on which said array of samples will reside lies directly opposite to the field of embedded optical features below and spaced from said surface.

24. The support of claim 1 carrying energy references.

25. The support of claim 24 in which the array-receiving area of said array-support surface is defined as a matrix of localized planar regions, at least one energy reference being associated with each of said localized regions.

26. The support of claim 24 in which at least some of said energy references comprise Kapton.

27. The support of claim 24 in which at least some of said energy references comprise labeled biological material.

28. The support of claim 24 in which at least some of said energy references comprise a selected glass or quartz.

29. The support of claim 1 constructed to launch an evanescent wave along said array-support surface.

30. The support of claim 1 constructed to guide one or more wave modes along said support surface.

31. The support of claim 1 constructed to cause the sample spots to function as Fabry Perot cavities during their absorption of energy.

32. The support of claim 1 carrying an array of sample spots.

33. The support of claim 32 wherein the sample spots are fluorescently labeled spots of biological material.

34. The support of claim 32 wherein the sample spots are of size between about 50 and 500 micron.

35. The support of claim 34 in which said embedded optical features are transmissive or reflective and have a size and periodicity of between about 1 and 50 micron.

36. The support of any of the claim 32 in which the spots have shape determined by being deposited as fluid spots from which liquid carrier has evaporated.

37. The support of claim 36 in which said spots are pin-deposited spots.

38. The support of claim 36 in which energy references associated with the sample spots comprise spots the shape of which has been determined by being deposited as fluid spots from which liquid carrier has evaporated.

39. The support of claim 1 disposed at an illumination and imaging station.

40. The support of claim 39 in which the imaging station includes a wide angle imaging system viewing the support surface along an axis normal to the support surface.

41. The support of claim 40 in which the imaging system is constructed to image an array area of about 15 mm by 15 mm.

42. The support of claim 41 in which the support is constructed of the general size and shape of a microscope slide, and said array-support area defines two areas to be imaged, each area of about 15×15 mm, and each associated with its respective field of said embedded optical features.

43. The support of claim 39 in which said imaging station comprises a stationary CCD camera.

44. The support of claim 43 in which said camera has a resolution of about 612×612 pixels.

45. The support of any claim 1 in which an imaging system is arranged over the array-support surface of the support and having a viewing axis normal to said surface.

46. The support 39 associated with a mirror constructed to operate with a broad beam light source, the mirror sized to direct the beam from the light source toward said support in a manner that the field of embedded optical features launch the radiation at said angle to said support surface.

47. The support of claim 46 associated with a tilt control mechanism capable of receiving tilt angle signals from a controlling computer and to direct the beam to said support, or move the support relative to the beam, at the commanded angles.

48. The support of claim 47 in which the tilt control mechanism has a range to change the angle of the beam reaching the support surface by about 30 degrees.

49. The support of claim 47 associated with a driver comprising a stepper motor and an elastic motion divider.

50. The support of claim 49 in which the stepper motor is a rotary stepper motor, and the elastic motion divider comprises a weak torsion spring driven by the rotary stepper motor, the weak spring driving a relatively stiff elastic torsional resistance, the mirror or support mounted in the region generally between the weak torsional spring and the torsional resistance so that the mirror is deflected by an angle substantially less than 10% of each step of the stepper motor.

51. The support claim 48 in which the mirror or the support is adapted to advance in steps of the order of 0.1 milliradian.

52. The support of claim 1 associated with an imaging system adapted to acquire a series of images over an angular range of illumination of the support, and to determine the results of imaging by comparing data obtained in each image.

53. The support of claim 52 in which the support carries energy references, and said comparison is based on the imaged results of those references at the various angles of illumination.

54. The support of claim 53 in which the support carries a matrix of energy references distributed over the image area, and localized regions for the final image are selected based upon the imaged results of references associated with localized regions in the respective images of the set, and a final image comprises a quilt formed of localized portions of the images selected from said set of images, or the sum of two or more localized portions.

55. The support of claim 1 in which the light source produces at the support at least a quasi-collimated beam, of not more than 5 degrees convergence or divergence.

56. The support of claim 55 in which the beam has no more than about 2 degrees convergence or divergence.

57. The support of claim 55 in which the light source comprises at least one array of light emitting diodes.

58. The support of claim 1 in which the beam is substantially collimated and the light source comprises at least one laser.

59. The support of claim 1 in which the light source comprises a multiplicity of selectable light source units whose outputs are merged into a single path leading to a mirror that directs the light to the support.

60. The support of any claim 1 having a matrix of energy references associated with the array support surface, and an imaging system adapted to produce image data normalized with respect to sensed results at said energy references.

* * * * *